United States Patent
Zhao et al.

(10) Patent No.: US 7,863,058 B2
(45) Date of Patent: *Jan. 4, 2011

(54) METHODS OF ATTACHING BIOLOGICAL COMPOUNDS TO SOLID SUPPORTS USING TRIAZINE

(75) Inventors: Chanfeng Zhao, San Diego, CA (US); Igor Kozlov, La Jolla, CA (US); Galina Steinberg-Tatman, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/364,286

(22) Filed: Feb. 2, 2009

(65) Prior Publication Data

US 2009/0137791 A1     May 28, 2009

Related U.S. Application Data

(60) Division of application No. 11/271,433, filed on Nov. 10, 2005, now Pat. No. 7,504,499, which is a continuation-in-part of application No. 10/739,959, filed on Dec. 17, 2003, now Pat. No. 7,259,258.

(51) Int. Cl.
*G01N 33/543* (2006.01)
*C07D 293/10* (2006.01)
*C12Q 1/68* (2006.01)
*A01N 37/18* (2006.01)
*C07H 19/04* (2006.01)
*C07K 2/00* (2006.01)

(52) U.S. Cl. .................. 436/518; 544/1; 544/2; 544/3; 544/186; 435/6; 514/1; 514/2; 536/26.6; 530/300

(58) Field of Classification Search ............ 514/1, 514/2; 435/6; 536/26.6; 530/300; 544/1, 544/2, 3, 186; 436/518
See application file for complete search history.

(56) References Cited

U.S. PATENT DOCUMENTS

| | | | |
|---|---|---|---|
| 4,469,863 A | 9/1984 | Ts'o et al. |
| 4,697,242 A | 9/1987 | Holland et al. |
| 4,935,877 A | 6/1990 | Koza |
| 5,034,506 A | 7/1991 | Summerton et al. |
| 5,216,141 A | 6/1993 | Benner |
| 5,235,033 A | 8/1993 | Summerton et al. |
| 5,386,023 A | 1/1995 | Sanghvi et al. |

(Continued)

FOREIGN PATENT DOCUMENTS

JP    2001 128697 A    5/2001

(Continued)

OTHER PUBLICATIONS

Beaucage et al., Tetrahedron 49(10): 1925 (1993).

(Continued)

*Primary Examiner*—Jezia Riley
(74) *Attorney, Agent, or Firm*—Knobbe Martens Olson & Bear LLP

(57) ABSTRACT

Disclosed are methods of attaching biologically active compounds to a solid surface, comprising modifying the solid surface using triazine chloride and attaching the biologically active compound to the triazine moiety.

23 Claims, 5 Drawing Sheets

U.S. PATENT DOCUMENTS

| | | | |
|---|---|---|---|
| 5,526,281 | A | 6/1996 | Champman et al. |
| 5,602,240 | A | 2/1997 | De Mesmaeker et al. |
| 5,637,684 | A | 6/1997 | Cook et al. |
| 5,664,048 | A | 9/1997 | Niemi et al. |
| 6,228,593 | B1 | 5/2001 | Lipshutz et al. |
| 6,326,147 | B1 | 12/2001 | Oldham et al. |
| 6,429,027 | B1 | 8/2002 | Chee et al. |
| 6,584,410 | B2 | 6/2003 | Berno |
| 6,925,389 | B2 | 8/2005 | Hitt et al. |
| 7,035,739 | B2 | 4/2006 | Schadt et al. |
| 7,107,155 | B2 | 9/2006 | Frudakis |
| 7,259,258 | B2 * | 8/2007 | Kozlov et al. ............... 544/1 |
| 7,504,499 | B2 * | 3/2009 | Zhao et al. ................. 544/1 |
| 2002/0059154 | A1 | 5/2002 | Rodvold |
| 2002/0102578 | A1 | 8/2002 | Dickinson et al. |
| 2004/0030503 | A1 | 2/2004 | Arough |

FOREIGN PATENT DOCUMENTS

| | | |
|---|---|---|
| WO | WO 01/16162 A | 3/2001 |
| WO | WO 2004/003234 | 1/2004 |

OTHER PUBLICATIONS

Brill et al., J. Am. Chem. Soc. 111:2321 (1989).
Carlsson et al., Nature 380:207 (1996).
Dempcy et al., Proc. Natl. Acad. Sci. USA 92:6097 (1995).
Egholm, J. Am. Chem. Soc. 114:1895 (1992).
Jeffs et al., Bioolecular NMR 34:17 (1994).
Jenkins et al., Chem. Soc. Rev. (1995) pp. 169-176.
Koshkin et al., J. Am. Chem. Soc. 120:13252-3 (1998).
Krchnak et al., 1996, "Synthetic Library Techniques: Subjective (Biased and Generic) Thoughts and Views," Molecular Diversity, 1:193-216.
Letsinger, J. Org. Chem. 35:3800 (1970).
Letsinger et al., Nucl. Acids Res. 14:3487 (1986).
Letsinger et al., J. Am. Chem. Soc. 110:4470 (1988).
Letsinger et al., Nucleoside & Nucleotide 13:1597 (1994).
Mag et al., Nucleic Acids Res. 19:1437 (1991).
Mesmaeker et al., Bioorganic & Medicinal Chem. Lett. 4:395 (1994).
Neilsen, Nature 365:566 (1993).
Nucleic Acid Research, 13:2399-2412 (1985).
Nucleic Acid Research, 14:7985-7994 (1986).
Nucleic Acid Research, 7:3131-3139 (1987).
Nucleic Acid Research, 15:6209-6224 (1987).
Nucleic Acid Research, 17:7179-7186 (1989).
Pauwels et al., Chemica Scripta 26:1411(1986).
Rawls, C&E News Jun. 2, 1997 p. 35.
Sawai et al., Chem. Lett. 805 (1984).
Sprinzl et al., Eur. J. Biochem. 81:579 (1977).
Tetrahedron Lett. 27:3991-3994 (1986).
Tetrahedron Lett. 28:2611-2614 (1987).
Tetrahedron Lett. 37;743 (1996).
Chapters 2&3, ASC Symposium Series 580, "Carbohydrate Modifications in Antisense Research", Ed Y.S. Sanghui and P. Dan Cook.
Masala, et al., *Organic Letters*, 1999, vol. 1 No. 9, pp. 1355-1357.
Beaucage, Serge L. and Radhakrishnan P. Iyer. "The Functionalization of Oligonucleotides Via Phosphoramidite Derivatives." Tetrahedron. 49.10 (1993): 1925-1963, 1993.
Dunagan, John and Santosh Vempala. "Optimal Outlier Removal in High-Dimensional Spaces." MIT Laboratory for Computer Science. (Mar. 2003): 317-318.
Egholm, Michael, et al. "PNA Hybridizes to Complementary Oligonucleotides Obeying the Watson-Crick Hydrogen-Bonding Rules." Nature, 365 (1993): 566-568.
Fan, JB., et al. "Highly parallel SNP Genotyping." Cold Spring Harbor Symposia on Quantitative Biology. 68 (2003): 69-78.
Hill, Andrew A., et al. Evaluation of Normalization Procedures for Oligonucelotide Array Data Based on Spiked cRNA Controls. Nov. 21, 2001, genome biology, vol. 2, No. 12, p. 1-13.
Liu, Wei-min, et al. "Algorithms for Large-Scale Genotyping Microarrays." Bioinformatics. 19.18 (2003): 2397-2403.
Shen, Richard, Jian-Bing Fan and Arnold Oliphant. "Optimization of Production-Scale Genotyping Assay Tutorial." Genetic Engineering News. Mar. 15, 2003, vol . 23, No . 6.
Tsukii, et al, "Development of an Automated SNP Analyzer." Furukawa Review, 24 (2003): 88-93.
Wang, Ena, et al. "A Strategy for Detection of Known and Unknown SNP Using a Minimum Number of Oligonucleotides Applicable in the Clinical Settings." Journal of Translational Medicine. 1 (2003): 1-14 (page numbers not for citation purposes).

* cited by examiner

METHODS OF ATTACHING BIOLOGICAL COMPOUNDS TO SOLID SUPPORTS USING TRIAZINE

RELATED APPLICATIONS

The present application is a divisional application of U.S. application Ser. No. 11/271,433 filed Nov. 10, 2005, by Zhao et al., and entitled "METHODS OF ATTACHING BIOLOGICAL COMPOUNDS TO SOLID SUPPORTS USING TRIAZINE" the entire disclosure of which is incorporated by reference herein, including any drawings, which is a continuation-in-part of U.S. application Ser. No. 10/739,959, filed on Dec. 17, 2003, by Kozlov et al., and entitled "METHODS OF ATTACHING BIOLOGICAL COMPOUNDS TO SOLID SUPPORTS USING TRIAZINE," the entire disclosure of which is incorporated by reference herein, including any drawings.

FIELD OF THE INVENTION

The present disclosure relates to the field of attachment of biologically active compounds, such as oligonucleotides and peptides, to solid surfaces.

BACKGROUND OF THE INVENTION

High-throughput analysis of oligonucleotides and peptides requires the immobilization of these compounds to solid surfaces. Various techniques exist in the art today for this purpose. However, these methods are cumbersome and achieve their task at considerable time and cost to the user. In addition, with many of the current methods, it is not possible to introduce different sequences onto the same solid surface at the same time.

SUMMARY OF THE INVENTION

Disclosed are methods of attaching biologically active compounds to a solid surface, comprising modifying the solid surface using triazine chloride and attaching the biologically active compound to the triazine moiety.

DETAILED DESCRIPTION OF THE PREFERRED EMBODIMENT

Figure 1:
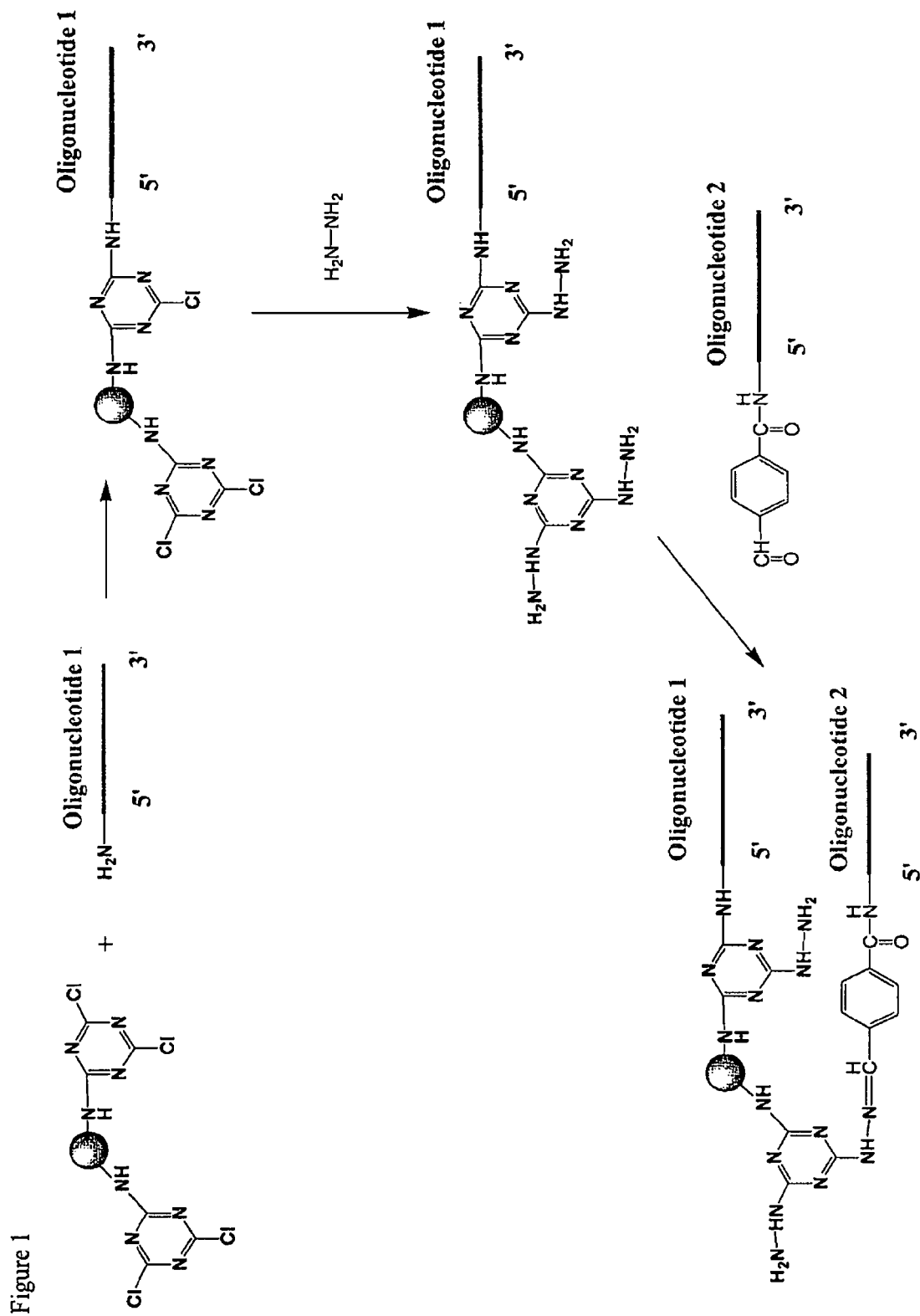
FIG. 1 is a schematic of the two-step reaction sequence for attaching two oligonucleotides to a bead.

In the first aspect, the present disclosure describes a compound of Formula I

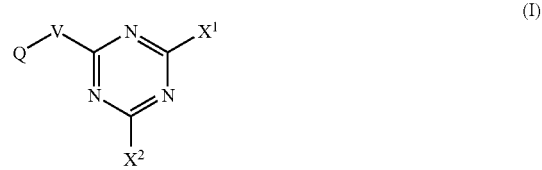

(I)

wherein $X^1$ and $X^2$ are each independently selected from the group consisting of chloro, NH—NH$_2$, NH—N=CH-E-T-L-D, wherein E is a bond or an electron withdrawing group;

T is selected from a bond, —C(O)—, —C(O)NH—, —NHC(O)—, an oxygen atom, a sulfur atom, NH, —S(O)—, —SO$_2$—, or alkyl substituted with one or more substituents selected from the group consisting of dialkylamine, NO$_2$, CN, SO$_3$H, COOH, CHO, alkoxy, and halogen;

L is a linker selected from the group consisting of a bond, —(CH$_2$)$_p$—, —(CH$_2$)$_p$—O—, —(CH$_2$)$_p$—C(O)—, —(CH$_2$)$_p$—C(O)NH—, (CH$_2$)$_p$—NHC(O)—, —(CH$_2$)$_p$—S(O)—, —(CH$_2$—CH$_2$—O)$_p$—, and —(CH$_2$)$_p$—S(O)$_2$—; and D is a biologically active polymer;

Q is a solid surface;

V is selected from a bond, NH, CO, NHCO, C(O)NH, (CH$_2$)$_p$, sulfur, and oxygen, or a combination thereof; and p is an integer greater than or equal to zero.

In certain embodiments, V is NH.

In some embodiments, E comprises an aryl, heteroaryl, heterocyclyl, alkyl, or cycloalkyl group.

In certain embodiments, E is a bond and T is a bond. Accordingly, in these embodiments, $X_1$ and $X_2$ are each independently NH—N=CH-E-D, where E and D are as defined above.

As used herein, the term "alkyl" refers to an aliphatic hydrocarbon group. The alkyl moiety can be a "saturated alkyl" group, which means that it does not contain any alkene or alkyne moieties. The alkyl moiety can also be an "unsaturated alkyl" moiety, which means that it contains at least one alkene or alkyne moiety. An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, can be branched, straight chain, or cyclic.

The alkyl group can have 1 to 20 carbon atoms (whenever it appears herein, a numerical range such as "1 to 20" refers independently to each integer in the given range; e.g., "1 to 20 carbon atoms" means that the alkyl group can consist of 1 carbon atom, 2 carbon atoms, 3 carbon atoms, etc., up to and including 20 carbon atoms, although the present definition also covers the occurrence of the term "alkyl" where no numerical range is designated). The alkyl group can also be a medium size alkyl having 1 to 10 carbon atoms. The alkyl group could also be a lower alkyl having 1 to 5 carbon atoms. The alkyl group of the compounds of the preferred embodiments can be designated as "$C_{1-n}$ alkyl" or similar designations, where n is an integer value. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Accordingly, alkyl or other moieties disclosed herein can alternatively have straight chain or branched structures.

The alkyl group can be substituted or unsubstituted. When substituted, the substituent group(s) is(are) one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substituent can be substituted with one of the above substituents.

In the present context, the term "cycloalkyl" is intended to cover three-, four-, five-, six-, seven-, or eight- or more membered rings comprising carbon atoms only. A cycloalkyl can optionally contain one or more unsaturated bonds situated in such a way, however, that an aromatic π-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

The term "heterocyclyl" is intended to mean three-, four-, five-, six-, seven-, and eight- or more membered rings wherein carbon atoms together with from 1 to 3 heteroatoms constitute the ring. A heterocyclyl can optionally contain one or more unsaturated bonds situated in such a way, however, that an aromatic π-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally also be fused to aryl rings, such that the definition includes bicyclic structures. Typically such fused heterocyclyl groups share one bond with an optionally substituted benzene ring. Examples of benzofused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Binding to the heterocycle can be at the position of a heteroatom or via a carbon atom of the heterocycle, or, for benzo-fused derivatives, via a carbon of the benzenoid ring.

In the present context the term "aryl" is intended to mean a carbocyclic aromatic ring or ring system. Moreover, the term "aryl" includes fused ring systems wherein at least two aryl rings, or at least one aryl and at least one $C_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from, but not limited to, heterocyclyl, heteroaryl, halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen.

Furthermore, in the present context, the term "heteroaryl" comprises fused ring systems wherein at least one heteroaryl ring shares at least one chemical bond with another carbocyclic ring. Thus, heteroaryl can include, for example, fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, $C_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

In certain embodiments, E is selected from the group consisting of

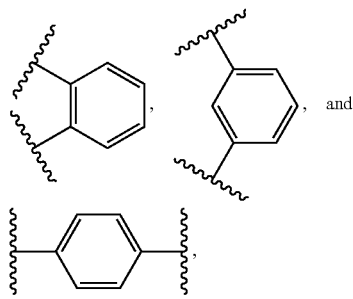

where the phenyl ring may be optionally substituted with one or more substituents selected, without limitation, from the group consisting of dialkylamine, $NO_2$, CN, $SO_3H$, COOH, CHO, alkoxy, and halogen.

In other embodiments, E is selected from the group consisting of —C(O)—, —S(O)—, —$SO_2$—, and alkyl optionally substituted with one or more substituents selected from the group consisting of dialkylamine, $NO_2$, CN, $SO_3H$, COOH, CHO, alkoxy, and halogen.

D can be a bioactive polymer as exemplified above, however D can be any of a variety of molecules including, for example, an organic molecule or a biologically active molecule or both. In certain embodiments, D is selected from the group consisting of a small organic molecule, a polymer, a macromolecule, an oligonucleotide, and a polypeptide. In certain embodiments, the oligonucleotide is selected from RNA, DNA, RNA having one or more non-naturally occurring bases, DNA having one or more non-naturally occurring bases. In other embodiments D is a polypeptide or a polypeptide having one or more non-naturally occurring amino acids. In particular embodiments, D can possess no known biological activity, the biological activity of D can be under investigation or the primary interest in D is not its biological activity.

As used herein, the terms "nucleic acid," "polynucleotide," or "oligonucleotide," and other grammatical equivalents, refer to at least two nucleotides covalently linked together. A nucleic acid of the preferred embodiments will generally contain phosphodiester bonds, although in some cases, as outlined below, nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989)), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl, 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C&E News Jun. 2, 1997 page 35. In addition nucleic acids include "locked nucleic acids" (LNAs) such as those described in Koshkin et al., J. Am. Chem. Soc. 120: 13252-3 (1998). LNA is a novel type of nucleic acid analog that contains a 2'-O, 4'-C methylene bridge. This bridge restricts the flexibility of the ribofuranose ring and locks the structure into a rigid bicyclic formation, conferring enhanced hybridization performance and exceptional biostability. Other useful nucleic acids are described in Khudyakov et al., Artificial DNA Methods and Applications CRC Press, NY 2003. All of these references are hereby expressly incorporated by reference.

The oligonucleotides useful in the molecules and methods described herein can have modified bases. Modified bases can comprise a moiety selected from, but not limited to, an aldehyde, a heterocyclic ring, a carbocyclic ring, an aryl ring, or a heteroaryl ring. Examples of modified bases include, but are not limited to, optionally substituted purines, optionally substituted pyrimidines, optionally substituted phenyl groups, optionally substituted naphthyl groups, optionally substituted pyridyl groups, and the like.

The oligonucleotides can have modified sugars. Exemplary sugar modifications for the oligonucleotide include sugars with six-membered rings. Other useful sugar modifications are described in Khudyakov et al., Artificial DNA Methods and Applications CRC Press, NY 2003.

Thus, the term "oligonucleotide" refers to an oligomer or polymer of nucleotides or mimetics thereof, This term includes oligonucleotides composed of naturally-occurring nucleobases, sugars and covalent internucleoside (backbone) linkages as well as oligonucleotides having non-naturally-occurring portions which function similarly. The term "oligonucleotide" can include nucleotides having a ribose or a deoxyribose. Similarly, the term "nucleotide" is used as recognized in the art to include natural bases, and modified bases well known in the art. Such bases are generally located at the 1' position of a sugar moiety. Nucleotide generally comprises a base, sugar and a phosphate group. The nucleotides can be unmodified or modified at the sugar, phosphate and/or base moiety. An oligonucleotide, polynucleotide or nucleic acid within the scope of the present disclosure can include, for example, at least 5, 7, 10, 12, 15, 17, 20, 25, 30, 35, 40, 50, 60, 70 or 80 or more nucleotides. These molecules can also be shorter having, for example, at most 80, 70, 60, 50, 40, 30, 20, 10, or 5 nucleotides. Nucleic acid molecules described herein can also have a length between any of these upper and lower limits.

Other molecules such as organic molecules having at least one carbon atom can be used in the molecules or methods described herein. "Small organic molecules" are molecules comprising at least one carbon atom and that have a molecular weight of less than 500 g/mol. Small organic molecules may be naturally occurring or be synthesized in a laboratory. In the context of the present disclosure, small organic molecules do not include polypeptides having more than two amino acids or oligonucleotides having more than 2 nucleotides. However, small organic molecules can comprise 1 or 2 amino acids, or 1 or 2 nucleotides. In certain embodiments, the small organic molecules are biologically active. In these embodiments, the small organic molecules may modulate the activity of an enzyme or may bind to a receptor in, or on the surface of, a cell. Certain of these molecules can be used as pharmaceuticals. In other embodiments, the small organic molecules possess no known biological activity, or that the primary interest in the molecule is not for its biological activity. An organic molecule useful for use in the methods or compounds described herein, such as a small organic molecule, can be a non-polymeric molecule such as a non-polypeptide or non-polynucleotide molecule.

"Polypeptides" or "peptides" refer to molecules that comprise two or more amino acids linked together through an amide or a peptide bond. The amino acids forming a polypeptide or peptide may be naturally occurring amino acids or non-naturally occurring amino acids. Naturally occurring amino acids are those that are typically L-amino acids and have α-side chains found in nature. Non-naturally occurring amino acids are amino acids that may be either an L or D isomer and have α-side chains not found in nature. Non-naturally occurring amino acids also include the D isomer of the naturally occurring amino acids. A polypeptide or peptide as described herein can include, for example, at least 5, 7, 10, 12, 15, 17, 20, 25, 30, 35, 40, 50, 60, 70 or 80 or more amino acids. These molecules can also be shorter having, for example, at most 80, 70, 60, 50, 40, 30, 20, 10, or 5 amino acids. Polypeptide molecules of the present disclosure can also have a length between any of these upper and lower limits.

In particular embodiments D can be a library or mixture of compounds. As demonstrated below in Example 4, a hydrazine treated solid phase substrate can be reacted with a mixture of polynucleotides to yield beads derivatized with a mixture of polynucleotides. Other mixtures can be used, such as a library of molecules. Libraries of molecules useful for the methods and compositions described herein can be obtained using, for example, well known methods of combinatorial synthesis built from any of a variety of building blocks. Exemplary building blocks and reagents are nucleic acids, amino acids, other organic acids, aldehydes, alcohols, and so forth, as well as bifunctional compounds, such as those given in Krchnak et al., 1996, "Synthetic library techniques; Subjective (biased and generic) thoughts and views," Molecular Diversity, 1: 193-216. A library that can be used in accordance with the present disclosure can also be obtained using recombinant methods with biological cells or cellular components.

The term "solid surface" is defined as a material having a rigid or semi-rigid surface to which a compound described herein can be attached or upon which they can be synthesized. As set forth above, Q can be a solid surface. A solid surface can be found on or in a solid-phase support or substrate. In certain embodiments, Q is selected from the group consisting of resin, microbead, glass, controlled pore glass (CPG), polymer support, membrane, paper, plastic, plastic tube or tablet, plastic bead, glass bead, slide, ceramic, silicon chip, multiwell plate, nylon membrane, fiber optic, and PVDF membrane. In certain embodiments, the solid surface Q may comprise functional groups, such as —$NH_2$, —OH, —SH, —COOH, etc., on its surface. In other embodiments, the surface of Q may be functionalized prior to the reaction with a triazine molecule. Other materials that can be used in accordance with the present disclosure include, but are not limited to, polypropylene, polyethylene, polybutylene, polyurethanes, nylon, metals, and other suitable materials. In some embodiments, the material is malleable or pliable, as discussed below. A solid surface can be a particle, for example, made of cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoriasol, carbon graphite, titanium dioxide, nylon, latex, or TEFLON®. "Microsphere Detection Guide" from Bangs Laboratories, Fishers, Inc., hereby incorporated by reference in its entirety, is a helpful guide. Further exemplary substrates within the scope of the present disclosure include, for example, those described in US Application Publication No. 02/0102578 and U.S. Pat. No. 6,429,027, both of which are incorporated herein by reference in their entirety, including any drawings.

In accordance with certain embodiments, one or more solid-phase supports, such as particles, can be securely attached to a second support or substrate thus being useful in high-throughput synthesis ("HTS") apparatus. In particular embodiments Q can be located at or in a particular feature of a solid-phase support substrate such as a well or depression. A solid phase support substrate can include one or more reaction vessels or wells. For example, Q can be a bead or other particle located in a well or depression or Q can be located at or in a feature of a substrate by virtue of being a part of the substrate itself. One or more solid-phase supports can be disposed within each well and affixed to the substrate. Such configuration allows synthetic reactions to be performed within one or more wells of the substrate. In particular, liquid reagents can be added to each well, reacted within each well, and then the residual liquid can removed from each well via centrifugation or aspiration. In one embodiment, the substrate is a microtiter plate that includes a plurality of wells disposed in arrays including, but not limited to, the rectangular array of wells disposed on a 96-well or 384-well microtiter plate.

As noted above, one or more solid-phase supports can be affixed to a substrate within each well. In some embodiments, the solid-phase supports are pressed and embedded into the substrate while the substrate is heated to an elevated temperature approximating the melting point of the substrate. As the substrate cools, the solid-phase supports are permanently bonded to the substrate, which bond is capable of withstanding the centrifugal forces often found in centrifugal separation. Alternatively, the solid phase support can be adhesively bonded to the internal diameter of the well utilizing a thermoplastic material having a relatively low melting point (i.e., lower than that of the substrate), a two-part epoxy, and/or other suitable means.

In particular embodiments, Q can be a chemical moiety or linker. Accordingly, the present disclosure includes soluble compounds having structures similar to those exemplified herein for solid substrates with the exception that the solid substrate can be replaced by any of a variety of known chemical moieties. The present disclosure further provides methods for adding a moiety to an aldehyde- or amine-containing compound or for linking together two aldehyde- or amine-containing compounds. By way of example, the methods disclosed herein can be used to synthesize a soluble compound of Formula VIII, X, XIII, XIV, or XVIII in which L is a linker. Q can be a linker selected from the group consisting of a bond, the moieties identified as L above, a polypeptide, a polynucleotide and any of a variety of other linkers known in the art. Thus, the present disclosure provides polypeptides attached to polynucleotides via triazine moieties, polypeptides attached to polypeptides via triazine moieties, polynucleotides attached to polynucleotides via triazine moieties and other combinations of polymers and/or organic molecules exemplified herein with respect to modification of solid surfaces. Further examples include, without limitation, attachment of antibodies to polynucleotides, attachment of enzymes to polynucleotides, attachment of organic molecules (for example in a combinatorial synthesis) to polynucleotides, and attachment of polysaccharides to polypeptides such as enzymes or antibodies.

In certain embodiments, p is an integer less than 50. In other embodiments, p is less than 30, while in other embodiments, p is less than 20. In some embodiments p is less than 10. In certain embodiments, p is greater than 2, while in other embodiments, p is greater than 5.

Certain embodiments of the present disclosure relate to a compound of Formula I in which E is

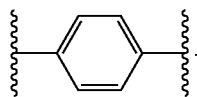

In other embodiments, T is —C(O)NH—. In still other embodiments, L is a bond, while in some other embodiments L is —(CH$_2$)$_p$—NHC(O)—. In some of these embodiments, p is 6. In yet other embodiments D is DNA, while in other embodiments D is a peptide.

In certain embodiments, the compound of Formula I is selected from the group consisting of

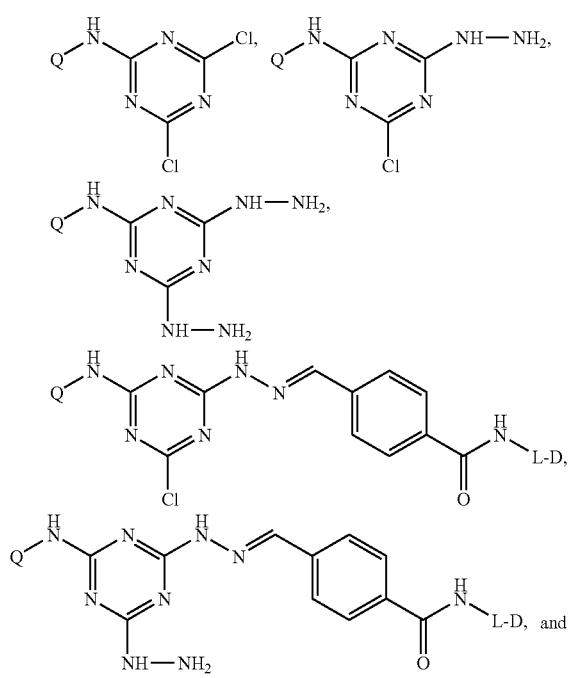

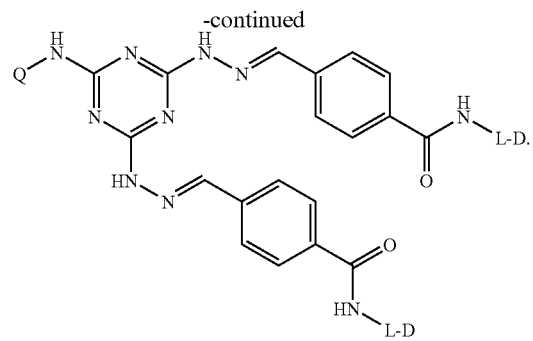

In another aspect, the present disclosure is related to the compound of Formula XX

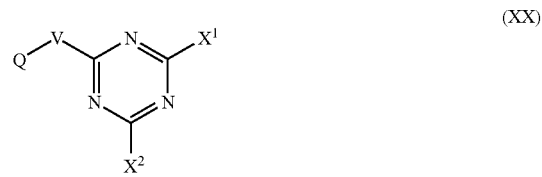

wherein

X$^1$ and X$^2$ are each independently selected from the group consisting of chloro, NH—NH$_2$, NH—N(X$^9$)(X$^{10}$), Z-D, NH—N=CH—Z-D, NH—N=Z-D, NH—NH—Z-D and NH—Z-D, wherein Z can be a bond or a linker; and D is a biologically active polymer;

X$^9$ and X$^{10}$ are each independently selected from the group consisting of alkyl, alkoxy, aryl, and heteroaryl, or X$^9$ and X$^{10}$ taken together along with the nitrogen atom to which they are attached form a five- or six-membered alicyclic, heterocyclic, aromatic, or heteroaromatic ring;

V is selected from a bond, SiO$_3$, NH, CO, NHCO, C(O)NH, (CH$_2$)$_p$, sulfur, and oxygen, or a combination thereof;

p is an integer greater than or equal to zero; and

Q is a solid surface.

In some embodiments, X$^1$ and X$^2$ are both chloro. In other embodiments, X$^1$ and X$^2$ are both NHNH$_2$. In other embodiments, one of X$^1$ and X$^2$ is chloro while the other of X$^1$ and X$^2$ is NHNH$_2$. In further embodiments, one of X$^1$ and X$^2$ is NHNH$_2$ while the other of X$^1$ and X$^2$ is NH—N=CH—Z-D.

In certain embodiments, D is selected from the group consisting of RNA, DNA, a polypeptide, RNA having one or more non-naturally occurring bases, DNA having one or more non-naturally occurring bases, and a polypeptide having one or more non-naturally occurring amino acids.

In some embodiments, D is DNA.

In some embodiments, V is NH, while in other embodiments, V is —NH—(CH$_2$)$_p$—Si(O)$_3$ where p is an integer greater than or equal to zero, such as p is 0, 1, 2, 3, 4, 5, 6, 7, 8, 9, or 10 or a number greater than 10.

In some embodiments, Q is selected from the group consisting of resin, microbead, glass, controlled pore glass (CPG), polymer support, membrane, paper, plastic, plastic tube or tablet, plastic bead, glass bead, slide, ceramic, silicon chip, multi-well plate, nylon membrane, and PVDF membrane.

The coupling between Z and D is broad and covers many different connections. In some embodiments, when D is a polynucleotide, Z can include the sugar, the phosphate and the base of the first nucleotide of the polynucleotide molecule. In other embodiments, Z can include only the sugar and the phosphate of the first nucleotide of the polynucleotide molecule. In still other embodiments, Z can include only the sugar of the first nucleotide of the polynucleotide molecule. In yet still other embodiments Z may include none of the sugar, the phosphate or the base of the first nucleotide of the polynucleotide molecule.

In another aspect, the present disclosure is related to a compound of Formula XVIII,

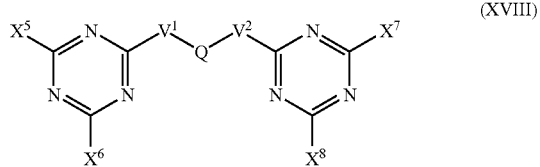

(XVIII)

wherein $X^5$, $X^6$, $X^7$, and $X^8$, are each independently selected from the group consisting of chloro, NH—NH$_2$, NH—N═CH-E-T-L-D, wherein each E is independently a bond or an electron withdrawing group;

each T is independently selected from a bond, —C(O)—, —C(O)NH—, —NHC(O)—, an oxygen atom, a sulfur atom, NH, —S(O)—, —SO$_2$—, or alkyl substituted with one or more substituents selected from the group consisting of dialkylamine, NO$_2$, CN, SO$_3$H, COOH, CHO, alkoxy, and halogen;

each L is independently a linker selected from the group consisting of a bond, —(CH$_2$)$_p$—, —(CH$_2$)$_p$—O—, —(CH$_2$CH$_2$O)$_p$, —(CH$_2$)$_p$—C(O)—, —(CH$_2$)$_p$—C(O)NH—, —(CH$_2$)$_p$—NHC(O)—, —(CH$_2$)$_p$—S(O)—, and —(CH$_2$)$_p$—S(O)$_2$—; and each D is independently a biologically active polymer;

Q is a solid surface;

$V^1$ and $V^2$ are each independently selected from a bond, NH, CO, NHCO, C(O)NH, (CH$_2$)$_p$, sulfur, and oxygen, or a combination thereof; and p is an integer greater than or equal to zero.

In another aspect, the present disclosure is related to the compound of Formula XXVI

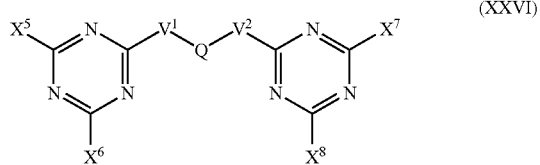

(XXVI)

where $X^5$, $X^6$, $X^7$, and $X^8$, are each independently selected from the group consisting of chloro, NH—NH$_2$, NH—N(X$^9$)(X$^{10}$), Z-D, NH—N═CH—Z-D, NH—N═Z-D, NH—NH—Z-D and NH—Z-D, where, each Z is a bond or a linker; and each D is independently a biologically active polymer;

$X^9$ and $X^{10}$ are each independently selected from the group consisting of alkyl, alkoxy, aryl, and heteroaryl, or $X^9$ and $X^{10}$ taken together along with the nitrogen atom to which they are attached form a five- or six-membered alicyclic, heterocyclic, aromatic, or heteroaromatic ring;

Q is a solid surface; and $V^1$ and $V^2$ are each independently selected from a bond, SiO$_3$ NH, CO, NHCO, C(O)NH, (CH$_2$)$_p$, sulfur, and oxygen, or a combination thereof; and p is an integer greater than or equal to zero.

Z can be any kind of chemical linker that can connect Formula XX or XXVI to the biologically active polymer D. Examples of Z include, but are not limited to, a bond, the moieties identified as L above, a polypeptide, a polynucleotide or any of a variety of other chemical linkers known in the art.

In some of the embodiments, all of the substituents D may be the same, while in other embodiments, all of the substituents D may be different. For example, a plurality of compounds disclosed herein having the same substituents D can be useful in a method of synthesizing a desired quantity of substituent D. An exemplary use of a plurality of compounds disclosed herein having different substituents D is the production of an array for use in a diagnostic application. Accordingly binding of a target analyte to a particular substituent D in an array of different substituents can identify a property of the target analyte or the sample from which it is derived. In yet other embodiments, some of the substituents D are the same while others are different. Embodiments include those in which each D is a peptide, while in other embodiments, each D is an oligonucleotide. When all of the substituents D are peptides or all are oligonucleotides, the sequence of the peptide or the oligonucleotide may be the same for all of the substituents D, or may be different for all of the substituents D, or may be the same for some of the substituents and different for other substituents. Accordingly, disclosed herein are oligonucleotide or peptide arrays.

In particular embodiments, a compound disclosed herein or a population of these compounds can include two or more types of molecules as substituents D. For example, the substituents D can include a polymer and a second molecule. In embodiments, where a population of molecules is used, each molecule can be associated with a polymer having a unique sequence such that the polymer encodes the identity of the molecule. For example, a unique oligonucleotide can be bound to each array location where a particular member of a population of second molecules is bound such that identification of the oligonucleotide sequence identifies the structure or other property of the molecule at the array location. The compounds and methods described herein can be used in known methods of encoding or decoding such as those described in WO 03/002979, WO 01/46675, and WO 99/67641, all of which are incorporated by reference herein in their entirety, including any drawings.

Thus, in some embodiments $X^5$ is peptide, while in other embodiments $X^6$ is peptide. In certain embodiments $X^7$ is peptide, while in still other embodiments $X^8$ is peptide. Similarly, in some embodiments $X^5$ is an oligonucleotide, while in other embodiments $X^6$ is an oligonucleotide. In certain embodiments $X^7$ is an oligonucleotide, while in still other embodiments $X^8$ is an oligonucleotide.

In another aspect, the present disclosure is related to a compound of the Formula XXI:

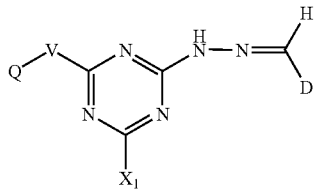
(XXI)

where

X$^1$ is selected from the group consisting of chloro and NH—NH$_2$; and

D is a biologically active polymer;

V is selected from a bond, SiO$_3$, NH, CO, NHCO, C(O)NH, (CH$_2$)$_p$, sulfur, and oxygen, or a combination thereof;

p is an integer greater than or equal to zero; and

Q is a solid surface.

In another aspect, the present disclosure is related to a compound of the Formula XXVII:

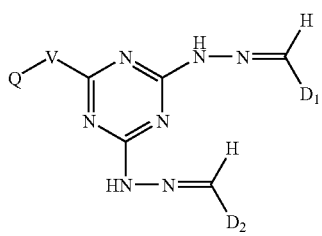
(XXVII)

where

X$^1$ is selected from the group consisting of chloro and NH—NH$_2$; and

D$_1$ and D$_2$ are the same or different biologically active polymers;

Q is a solid surface;

V is selected from the group consisting of a bond, SiO$_3$, NH, CO, NHCO, C(O)NH, (CH$_2$)$_p$, sulfur, and oxygen, or a combination thereof; and p is an integer greater than or equal to zero.

In another aspect disclosed herein is a method of synthesizing a compound of Formula XXVII

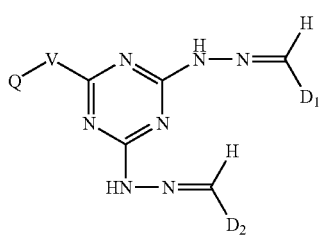
(XXVII)

wherein

D1 and D2 are the same or different biologically active polymers, Q is a solid surface, X$^1$ is chloro or —NHNH$_2$, and V is selected from the group consisting of a bond, SiO$_3$, NH, CO, NHCO, C(O)NH, (CH$_2$)$_p$, sulfur, and oxygen, or a combination thereof; and p is an integer greater than or equal to zero;

comprising:

silanating a solid surface with a silanating compound or providing a solid surface having at least one group reactive towards cyanuric chloride;

reacting the solid surface with cyanuric chloride and hydrazine to obtain a compound of Formula XXII

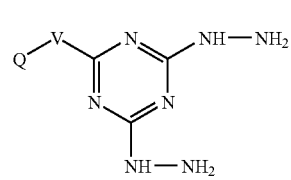
(XXII)

wherein Q is a solid surface and V is selected from the group consisting of a bond, SiO$_3$, NH, CO, NHCO, C(O)NH, (CH$_2$)$_p$, sulfur, and oxygen, or a combination thereof; and p is an integer greater than or equal to zero; and reacting the compound of Formula XXII with one or more aldehyde modified biologically active polymers to obtain a compound of Formula XXVII.

Some solid surfaces already exhibit groups on the surface, which can react with a cyanuric chloride compound. For example, glass has —OH groups on the surface, which is reactive towards cyanuric chloride. The hydroxyl group can substitute the chloro to form an ether linkage. Other solid surfaces do not naturally have a group that is reactive towards cyanuric chloride. These solid surfaces can be modified by reacting the solid surface with a reagent that attaches a group that is reactive towards cyanuric chloride on the surface.

In some embodiments, the group that is reactive towards cyanuric chloride is a nucleophile. In certain embodiments, the nucleophile is selected from the group consisting of hydrazine, amine, thiol, and hydroxyl.

In yet another aspect, the present disclosure is related to a compound wherein the compound of Formulas XX is selected from the group consisting of:

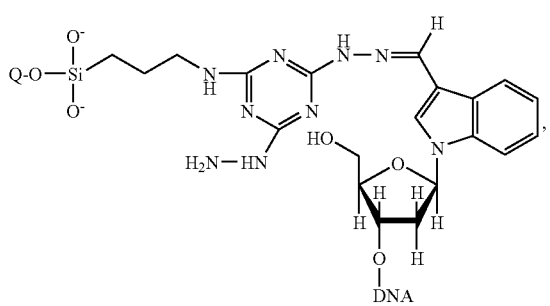

-continued

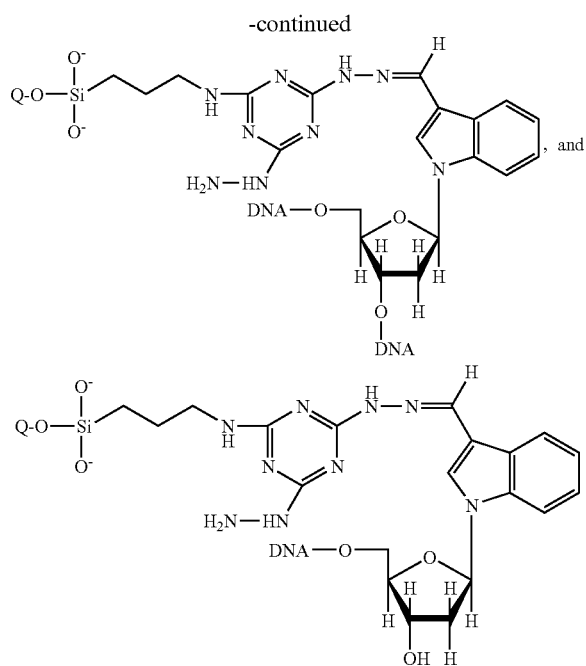

wherein Q is a solid surface.

In another aspect, disclosed herein is a method of synthesizing a compound of Formula I

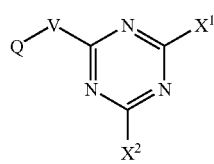

(I)

wherein $X^1$ is Cl and $X^2$ is NH—NH$_2$ or $X^1$ and $X^2$ are both NH—NH$_2$ and Q is a solid surface, and V is selected from a bond, NH, CO, NHCO, C(O)NH, (CH$_2$)$_p$, sulfur, and oxygen, or a combination thereof;

comprising reacting a solid surface having —NH$_2$, —COH, —COOH, —NHCOH, —NHCOOH, —C(O)NH$_2$, —(CH$_2$)$_p$CH$_3$, —SH, or —OH, or a combination thereof, on its surface with triazine chloride to obtain a compound of Formula III

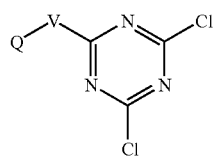

(III)

reacting the compound of Formula III with hydrazine to obtain a compound of Formula I.

The solid surfaces can have any of a variety of different reactive groups, including, but not limited to, —NH$_2$, —OH, —SH, or —NHNH$_2$. Some of the conditions for reacting a solid surface having —NH$_2$ with triazine chloride are provided in Example 1 below. Similar solvents and conditions can be used for solid surfaces having other reactive groups. Those skilled in the art will know or be able to determine appropriate solvents and conditions based on known properties of the particular reactive group being used.

Examples of solvents for reactions involving hydrazine, triazines or other compounds disclosed herein include, but are not limited to, acetonitrile, acetone, n-butyl acetate, carbon tetrachloride, chlorobenzene, chloroform, cyclohexane, cyclopentane, dimethyl acetamide, dimethyl formamide, dimethyl sulfoxide, dioxane, ethyl acetate, ethyl ether, ethylene dichloride, heptane, hexadecane, iso-octane, methyl t-butyl ether, methyl ethyl ketone, methyl isoamyl ketone, methyl isobutyl ketone, methyl n-propyl ketone, methylene chloride, n-methylpyrrolidone, pentane, petroleum ether, pyridine, tetrahydrofuran, toluene, 1,2,4-trichlorobenzene, trichloroethylene, trichlorotrifluoroethane, o-xylene and mixtures thereof.

A compound of Formula I is useful for derivatizing a surface Q with a second compound having an aldehyde. The aldehyde can react with the distal amine of an NH—NH$_2$ moiety to form an imine linkage between the compound of Formula I and the second compound. Thus, in cases where Q of Formula I is a solid surface the present disclosure provides a method for immobilizing a compound having a reactive aldehyde moiety. In particular embodiments, aldehydes used in a methods described herein for the synthesis of compounds described herein will have an electron withdrawing group including, but not limited to

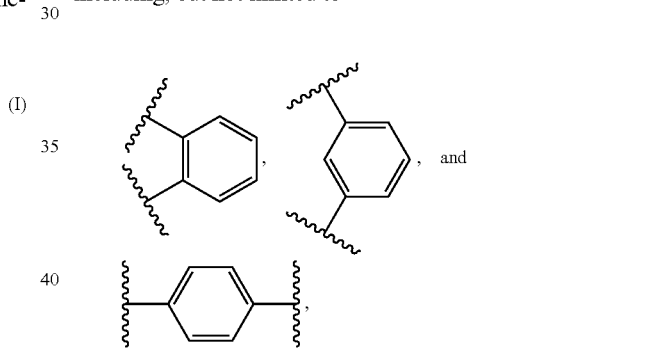

where the phenyl ring may be optionally substituted with one or more substituents selected, without limitation, from the group consisting of dialkylamine, NO$_2$, CN, SO$_3$H, COOH, CHO, alkoxy, and halogen.

In another aspect, the present disclosure is related to a method of synthesizing a compound of Formula XXII

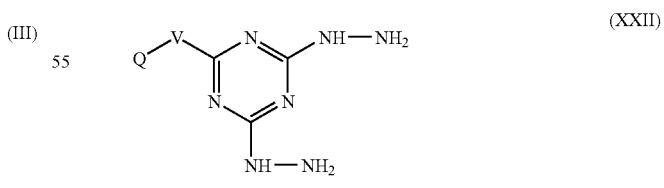

(XXII)

wherein Q is a solid surface and V is selected from a bond, SiO$_3$, NH, CO, NHCO, C(O)NH, (CH$_2$)$_p$, sulfur, and oxygen, or a combination thereof; and p is an integer greater than or equal to zero;

comprising: silanating a solid surface with a silanating compound, reacting the silanated solid surface with cyanuric chloride and hydrazine to obtain a compound of Formula XXII.

As used herein, the terms "silanating" and "silanizing" refers broadly to attaching any silicon-containing compound to another compound, surface or substrate. Examples of silanating compounds include, but are not limited to aminopropyltrimethoxysilane, γ-aminopropyltriethoxysilane, dimethylchlorosilane, and the like. A compound thus reacted is referred to as a "silanated" or "silanized" compound.

In another aspect, disclosed herein is a method of synthesizing a compound of Formula II

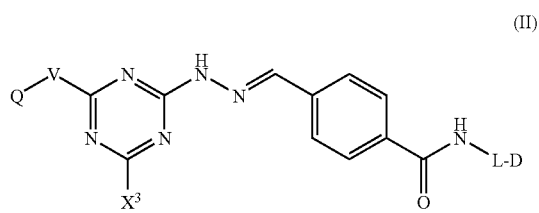

(II)

wherein

D is a biologically active polymer, Q is a solid surface, $X^3$ is chloro or —$NHNH_2$, and V is selected from a bond, NH, CO, NHCO, C(O)NH, $(CH_2)_p$, sulfur, and oxygen, or a combination thereof;

comprising reacting a solid surface having —$NH_2$, —COH, —COOH, —NHCOH, —NHCOOH, —C(O)$NH_2$, —$(CH_2)_p CH_3$, —SH, or —OH, or a combination thereof, on its surface with triazine chloride to obtain a compound of Formula III

(III)

reacting the compound of Formula III with hydrazine and a compound of Formula V

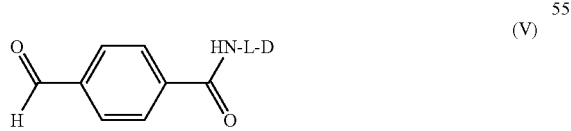

(V)

to obtain a compound of Formula II.

In certain embodiments, reacting the compound of Formula III with hydrazine results in the formation of a compound of Formula IV, while in other embodiments, this reaction results in compound of Formula VII.

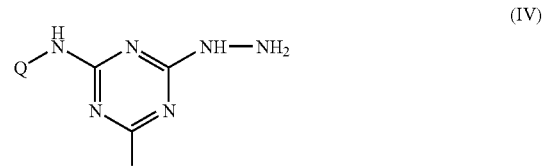

(IV)

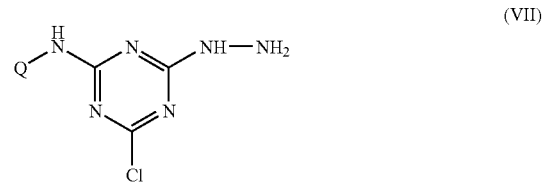

(VII)

Thus, in some embodiments hydrazine replaces both chlorides in the compound of Formula III, whereas in other embodiments, hydrazine replaces only one of the chloride substituents. For example, one molar equivalent or less of hydrazine can be reacted with a compound of Formula III in order to form a compound of Formula VII. Alternatively, a two or more fold molar excess of hydrazine can be reacted with a compound of Formula III in order to form a compound of Formula IV.

In another aspect, the present disclosure refers to a method of synthesizing a compound of Formula XXI

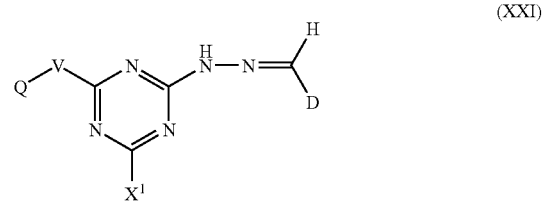

(XXI)

where

D is a biologically active polymer, $X^1$ is chloro or —$NHNH_2$, and V is selected from a bond, $SiO_3$, NH, CO, NHCO, C(O)NH, $(CH_2)_p$, sulfur, and oxygen, or a combination thereof, p is an integer greater than or equal to zero; and Q is a solid surface;

comprising:

silanating a solid surface with a silanating compound, reacting the silanated solid surface with cyanuric chloride and hydrazine to obtain a compound of Formula XXII

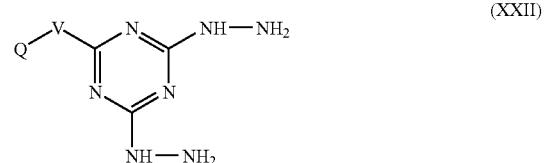

(XXII)

reacting the compound of Formula XXII with an aldehyde modified biologically active polymer to obtain a compound of Formula XXI.

In some embodiments, the aldehyde modified biologically active polymer can be selected from the group consisting of RNA, DNA, a polypeptide, RNA having one or more non-naturally occurring bases, DNA having one or more non-naturally occurring bases, and a polypeptide having one or more non-naturally occurring amino acids.

As used herein "aldehyde modified biologically active polymer" refers to a biologically active polymer which has an aldehyde on one or more of its substituents. This includes any location on such a polymer and the polymer can be in any state of polymerization or can exist as a single monomer of the polymer. In some embodiments, the aldehyde modified biologically active polymer is modified on the 5' end of a DNA or RNA molecule. In other embodiments, the aldehyde modified biologically active polymer is modified on the 3, end of the DNA or RNA molecule. In some embodiments, the aldehyde modified biologically active polymer is modified on the C-terminal of a polypeptide. In other embodiments, the aldehyde modified biologically active polymer is modified on the N-terminal of a polypeptide. In some embodiments, the aldehyde modified biologically active polymer is modified on the base of the first nucleotide of a polynucleotide.

In certain embodiments, the modified base on the aldehyde modified biologically active polymer has the following structure:

wherein D is a biologically active polymer.

In other embodiments, the aldehyde modified biologically active polymer has the structure of the compound of Formula XXIII:

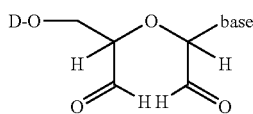

(XXIII)

In these embodiments, the compound of Formula XXIII reacts with the hydrazinyl moiety on the compound of Formula XXII, thereby forming a substituted morpholin, which has the result of attaching the biologically active polymer to the solid surface. The reaction is depicted in the following scheme.

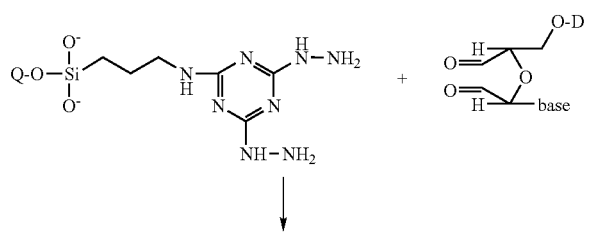

-continued

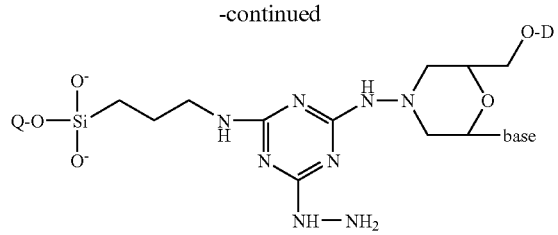

In some embodiments, the silanating compound can be R—Si(OR')$_3$, R$_1$(R$_2$)—Si—(OR')$_2$ or R$_1$(R$_2$)(R$_3$)—Si—(OR'). In certain embodiments, the R, R$_1$, R$_2$, and R$_3$ group of the silanating compound can each independently contain any or a combination of —NH—, —(CH$_2$)$_p$—, —C(O)— and —O—, wherein p is an integer greater than or equal to zero. In some embodiments, R, R$_1$, R$_2$, and R$_3$ are each independently selected from optionally substituted alkyl optionally substituted aryl, optionally substituted alkoxy, and optionally substituted aryloxy. R' can be hydrogen, optionally substituted alkyl, optionally substituted aryl, optionally substituted alkoxy, or optionally substituted aryloxy. In some embodiments, the silanating compound is aminopropyltrimethoxysilane.

Thus, in some embodiments, a solid surface, such as a silica bead, glass bead, resin, or any other solid surface disclosed herein, is silanized by a silanating compound. The silanating compound preferably contains an alkylamino group attached to the silicon atom such that, following silanization, an alkylamino group, having a primary amino group, is attached to the solid surface. The modified solid surface is then reacted with cyanuric chloride to obtain a compound of Formula III, where V is an aminoalkylsilane group. The cyanuric activated solid surface is then reacted with hydrazine to replace the remaining two chloro substituents on the cyanuric group with hydrazinyl moieties. Aldehyde modified oligonucleotides are then reacted with modified solid surface. The aldehyde moiety of the oligonucleotide molecule reacts with the hydrazinyl moiety on the solid surface, thereby attaching the oligonucleotide to the solid surface and immobilizing it.

Another aspect of the present disclosure refers to a method of synthesizing a compound of the Formula XXV

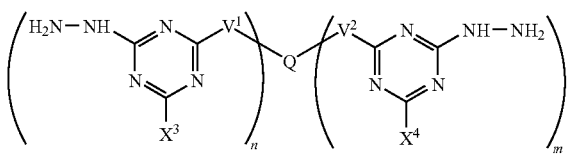

(XXV)

where
Q is a solid surface;
V$_1$ and V$_2$ are selected from a bond, NH, CO, NHCO, C(O)NH, (CH$_2$)$_p$, sulfur, SiO$_3$ and oxygen, or a combination thereof;
X$^3$ and X$^4$ are each independently chloro or —NH—NH$_2$, and p is an integer greater than or equal to zero;

comprising:
silanating a solid surface with a silanating compound, and reacting the silanated solid surface with cyanuric chloride and hydrazine to obtain the compound of Formula XXV.

Another aspect of the present disclosure refers to a method of obtaining a solid surface to which a plurality of biologically active polymers are attached, and having a structure of Formula XXIV,

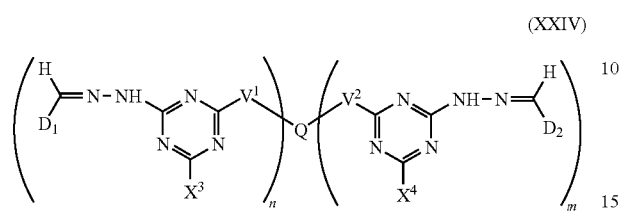

where

- $D_1$ is a biologically active polymer having a first primary sequence;
- $D_2$ is a biologically active polymer having a second primary sequence;
- where the first primary sequence and the second primary sequence may be the same or different;
- Q is a solid surface;
- $X^3$ and $X^4$ are each independently chloro or —NH—$NH_2$;
- n and m are each independently 1 or an integer greater than 1; and
- $V^1$ and $V^2$ are selected from a bond, NH, CO, NHCO, C(O)NH, $(CH_2)_p$, sulfur, $SiO_3$ and oxygen, or a combination thereof; and
- p is an integer greater than or equal to zero comprising:

providing a compound of Formula XXV

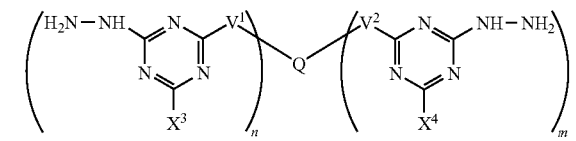

and reacting a compound of Formula XXV with one or more aldehyde modified biologically active polymers to obtain the compound of Formula XXIV.

In yet another aspect, disclosed herein is a method of synthesizing a compound of Formula II

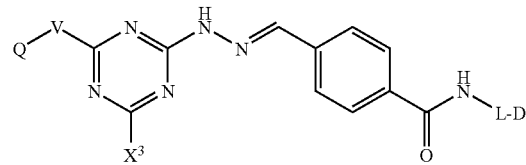

wherein

D is a biologically active polymer, Q is a solid surface, $X^3$ is chloro or —$NHNH_2$, and V is selected from a bond, NH, CO, NHCO, C(O)NH, $(CH_2)_p$, sulfur, and oxygen, or a combination thereof, comprising providing a compound of Formula III

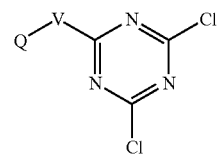

reacting the compound of Formula III with hydrazine and a compound of Formula V

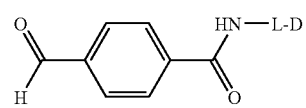

to obtain a compound of Formula II.

In certain embodiments, V is NH.

The methods of synthesis described above relate to single attachment chemistry, i.e., methods of synthesis where only a single type of substituent D is to be attached to the solid surface. There are times when it is desirable to attach two or more different types of substituent D to a single solid surface.

Thus, in another aspect, disclosed herein is a method of obtaining a solid surface to which a plurality of biologically active polymers are attached, and having a structure of Formula XIII,

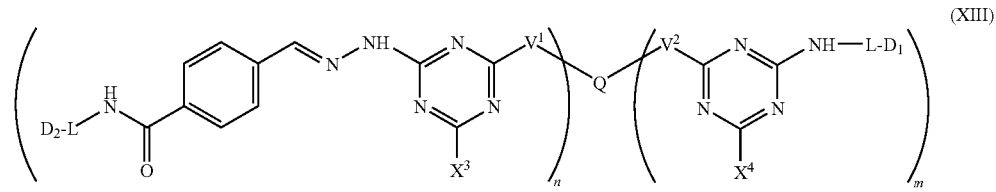

wherein L is a linker selected from the group consisting of a bond, —(CH$_2$)$_p$—, —(CH$_2$)$_p$—O—, —(CH$_2$)$_p$—C(O)—, —(CH$_2$)$_p$—C(O)NH—, —(CH$_2$)$_p$—NHC(O)—, —(CH$_2$)$_p$—S(O)—, —(CH$_2$—CH$_2$—O)$_p$—, and —(CH$_2$)$_p$—S(O)$_2$—, wherein p is an integer greater than or equal to zero; and $D_1$ is a biologically active polymer having a first primary sequence;

$D_2$ is a biologically active polymer having a second primary sequence;

wherein said first primary sequence and said second primary sequence may be the same or different;

Q is a solid surface;

$X^3$ and $X^4$ are each independently chloro or —NH—NH$_2$;

$V^1$ and $V^2$ are each independently selected from a bond, NH, CO, NHCO, C(O)NH, (CH$_2$)$_p$, sulfur, and oxygen, or a combination thereof; and n and m are each independently 1 or an integer greater than 1;

comprising:

reacting a solid surface having —NH$_2$, —CHO, —COOH, —NHCOH, —NHCOOH, —C(O)NH$_2$, —(CH$_2$)$_p$CH$_3$, —SH, or —OH, or a combination thereof, on its surface with triazine chloride to obtain a compound of Formula VIII

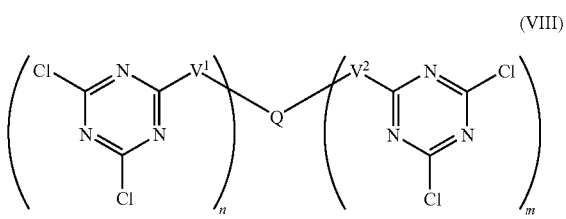

(VIII)

reacting the compound of Formula VIII with a compound of Formula IX

H$_2$N-L-D$_1$ (IX)

to obtain a compound of Formula X

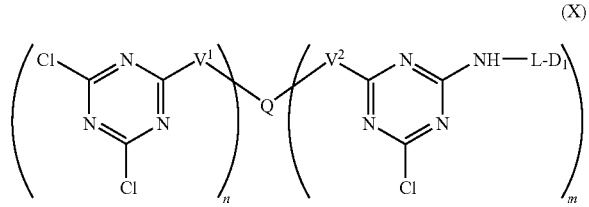

(X)

reacting the compound of Formula X with hydrazine and a compound of Formula XII

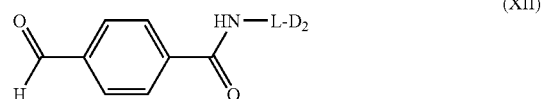

(XII)

to obtain a compound of Formula XIII.

An amine compound disclosed herein can be obtained commercially or synthesized using methods known in the art. For example, a nucleic acid can be derivatized to include an amino group using methods described in Nucleic Acid Research, 13: 2399-2412 (1985); Nucleic Acid Research, 14; 7985-7994 (1986); Tetrahedron Letters, 27:3991-3994 (1986); Nucleic Acid Research, 7:3131-3139 (1987); Nucleic Acid Research, 15; 6209-6224 (1987); Tetrahedron Letters, 28:2611-2614 (1987); or Nucleic Acid Research, 17: 7179-7186 (1989). Such methods can be used with conventional equipment or, if desired, high throughput methods can employ robotic devices. In embodiments using robotics or other equipment for manipulations of the reactions, solvents for the reactions can be replaced with those that are compatible with the equipment such as acetonitrile or other inert solvent.

Reactions between amine compounds or aldehyde compounds and triazines can be carried out in the presence of salts if desired. Exemplary salts that are useful include, but are not limited to sodium chloride, lithium chloride, magnesium chloride, potassium chloride, sodium sulfate, lithium sulfate, magnesium sulfate, potassium sulfate, or salts of phosphate or acetate. Salts can be present in concentrations of 0.01, 0.05, 0.1, 0.5, 1, 2, 3, 4, or 5 M or higher.

A "primary sequence" is the sequence of amino acids in a polypeptide or a sequence of nucleotides in an oligonucleotide.

In certain embodiments, $D_1$ or $D_2$ is an organic molecule, such as a small organic molecule, instead of a biologically active polymer. In some embodiments, both $D_1$ and $D_2$ are organic molecules. In these embodiments, $D_1$ and $D_2$ can be two different molecules.

In certain embodiments, $V^1$ and $V^2$ are each NH. In some embodiments, $D_1$ and $D_2$ are both peptides, while in other embodiments $D_1$ and $D_2$ are both oligonucleotides. In yet other embodiments, $D_1$ is a peptide and $D_2$ is an oligonucleotide. As set forth previously herein, $D_1$ or $D_2$ can independently be a polymer, such as a polypeptide or polynucleotide, or an organic molecule or any of a variety of combinations thereof.

In another aspect, the present disclosure relates to a method of obtaining a solid surface to which a plurality of biologically active polymers are attached, and having a structure of Formula XIII,

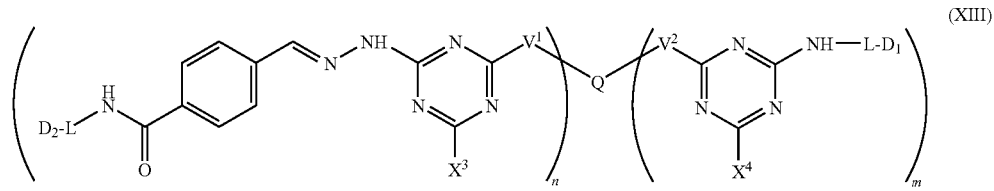

(XIII)

wherein L is a linker selected from the group consisting of a bond, —(CH$_2$)$_p$—, —(CH$_2$)$_p$—O—, —(CH$_2$)$_p$—C(O)—, —(CH$_2$)$_p$—C(O)NH—, —(CH$_2$)$_p$—NHC(O)—, —(CH$_2$)$_p$—S(O)—, —(CH$_2$—CH$_2$—O)$_p$—, and —(CH$_2$)$_p$—S(O)$_2$—, wherein p is an integer greater than or equal to zero; and D$_1$ is a biologically active polymer having a first primary sequence;

D$_2$ is a biologically active polymer having a second primary sequence;

wherein said first primary sequence and said second primary sequence may be the same or different;

Q is a solid surface;

X$^3$ and X$^4$ are each independently chloro or —NH—NH$_2$;

V$^1$ and V$^2$ are each independently selected from a bond, NH, CO, NHCO, C(O)NH, (CH$_2$)$_p$, sulfur, and oxygen, or a combination thereof; and n and m are each independently 1 or an integer greater than 1;

comprising:

providing a compound of Formula VIII

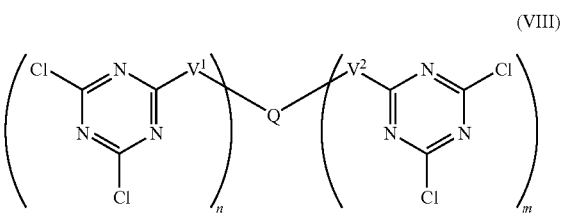

(VIII)

reacting the compound of Formula VIII with a compound of Formula IX

H$_2$N-L-D$_1$ (IX)

to obtain a compound of Formula X

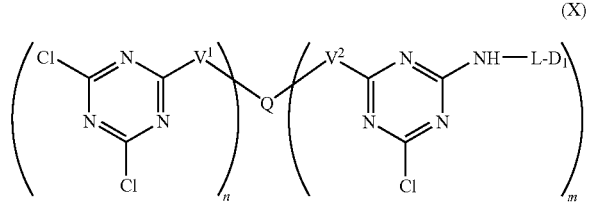

(X)

reacting the compound of Formula X with hydrazine and a compound of Formula XII

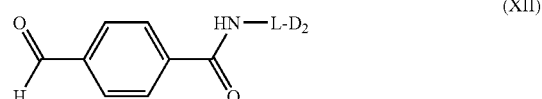

(XII)

to obtain a compound of Formula XIII.

An embodiment relating to the above methods is depicted in FIG. 1. As shown in the figure, a bead to which at least two molecules of triazine chloride are attached reacts with an amine-modified oligonucleotide (Oligonucleotide 1). The resulting complex is then reacted with hydrazine, whereby the chloride substituents on the triazine moieties are replaced by hydrazine. The product is then reacted with an aldehyde-modified oligonucleotide (Oligonucleotide 2). The amine-modified oligonucleotide selectively reacts with a chloro-substituted triazine, while the aldehyde-modified oligonucleotide selectively reacts with the hydrazine-substituted triazine. Thus, in two simple steps, two different oligonucleotides are attached to the solid surface.

While FIG. 1 and the above discussion relate to oligonucleotides, it should be understood that the above procedure can be easily modified to attach other types of compounds, such as peptides or small organic molecules, to triazine-modified solid surfaces. Thus, generally, in the first step, an amine-modified compound is reacted with the triazine chloride-modified solid surface. The resulting complex is then reacted with hydrazine, whereby the chloride substituents on the triazine moieties are replaced by hydrazine. The product is then reacted with an aldehyde-modified compound to obtain the final product. Those skilled in the art will recognize that a compound being reacted in the first step should not contain reactive amines other than the amine desired to participate in the reaction with the triazine chloride-modified solid surface. Similarly, a compound being reacted in the second step should not contain a reactive aldehyde group other than the one desired to participate in the reaction with the hydrazine treated, triazine chloride-modified solid surface. In embodiments where amine or aldehyde reactive groups are present in a compound used in the present disclosure, but are not desired to participate in a particular reaction, the reactive groups can be selectively blocked from participating in the reactions using a blocking group or a protecting group. Those skilled in the art will know or be able to determine appropriate protecting group chemistry based on the properties of the compound used. For example, common protected forms of aldehydes and amines can be found in Greene and Wuts *Protective Groups in Organic Synthesis*; John Wiley and Sons, New York, 1991.

In a further aspect, disclosed is a method of obtaining a solid surface to which a plurality of biologically active polymers are attached, and having a structure of Formula XIV,

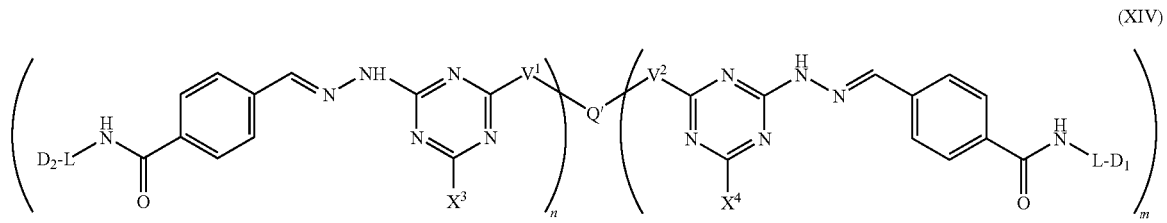

(XIV)

wherein L is a linker selected from the group consisting of a bond, —(CH$_2$)$_p$—, —(CH$_2$)$_p$—O—, —(CH$_2$)$_p$—C(O)—, —(CH$_2$)$_p$—C(O)NH—, —(CH$_2$)$_p$—NHC(O)—, —(CH$_2$)$_p$—S(O)—, —(CH$_2$—CH$_2$—O)$_p$—, and —(CH$_2$)$_p$—S(O)$_2$—, wherein p is an integer greater than or equal to zero; and D$_1$ is a biologically active polymer having a first primary sequence;

D$_2$ is a biologically active polymer having a second primary sequence;
wherein said first primary sequence and said second primary sequence may be the same or different;

Q is a solid surface;

X$^3$ and X$^4$ are each independently chloro or —NH—NH$_2$;

V$^1$ and V$^2$ are each independently selected from a bond, NH, CO, NHCO, C(O)NH, (CH$_2$)$_p$, sulfur, and oxygen, or a combination thereof; and n and m are each independently 1 or an integer greater than 1;

comprising:
reacting a solid surface having —NH$_2$, —COH, —COOH, —NHCOH, —NHCOOH, —C(O)NH$_2$, —(CH$_2$)$_p$CH$_3$, —SH, or —OH, or a combination thereof, on its surface with triazine chloride to obtain a compound of Formula VIII

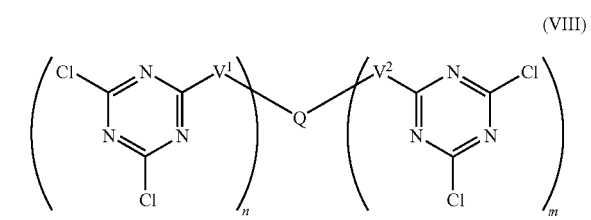

(VIII)

reacting a compound of Formula VIII with hydrazine and compounds of Formulae XVI and XVII

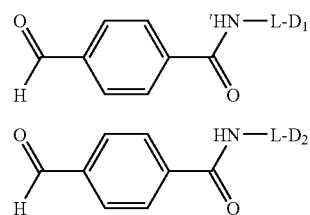

(XVI)

(XVII)

to obtain a compound of Formula XIV.

Further aspects of the present disclosure include a method of obtaining a solid surface to which a plurality of biologically active polymers are attached, and having a structure of Formula XIV,

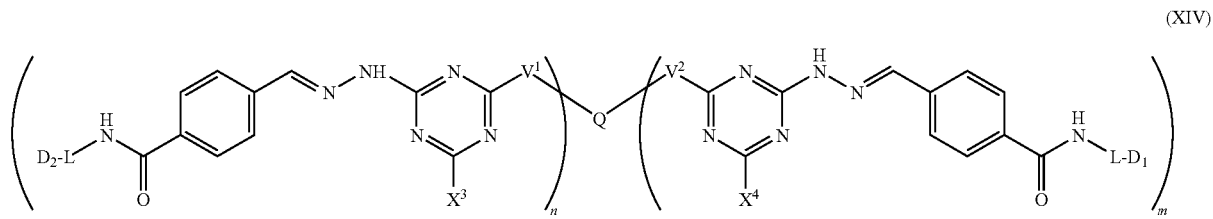

(XIV)

wherein L is a linker selected from the group consisting of a bond, —(CH$_2$)$_p$—, —(CH$_2$)$_p$—O—, —(CH$_2$)$_p$—C(O)—, —(CH$_2$)$_p$—C(O)NH—, —(CH$_2$)$_p$—NHC(O)—, —(CH$_2$)$_p$—S(O)—, —(CH$_2$—CH$_2$—O)$_p$—, and —(CH$_2$)$_p$—S(O)$_2$—, wherein p is an integer greater than or equal to zero; and D$_1$ is a biologically active polymer having a first primary sequence;

D$_2$ is a biologically active polymer having a second primary sequence;
wherein said first primary sequence and said second primary sequence may be the same or different;

Q is a solid surface;

X$^3$ and X$^4$ are each independently chloro or —NH—NH$_2$; and n and m are each independently 1 or an integer greater than 1;

comprising:
providing a compound of Formula VIII

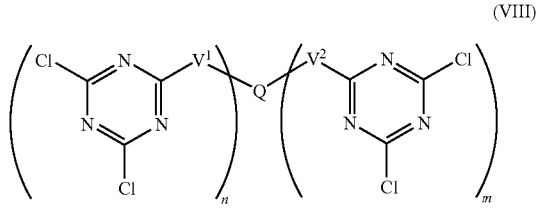

(VIII)

reacting a compound of Formula VIII with hydrazine and compounds of Formulae XVI and XVII

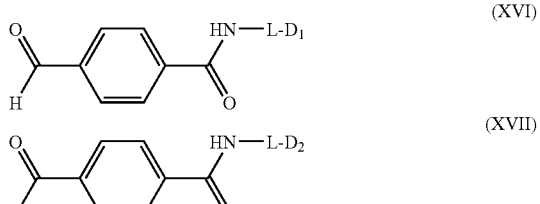

(XVI)

(XVII)

to obtain a compound of Formula XIV.

Figure 2:
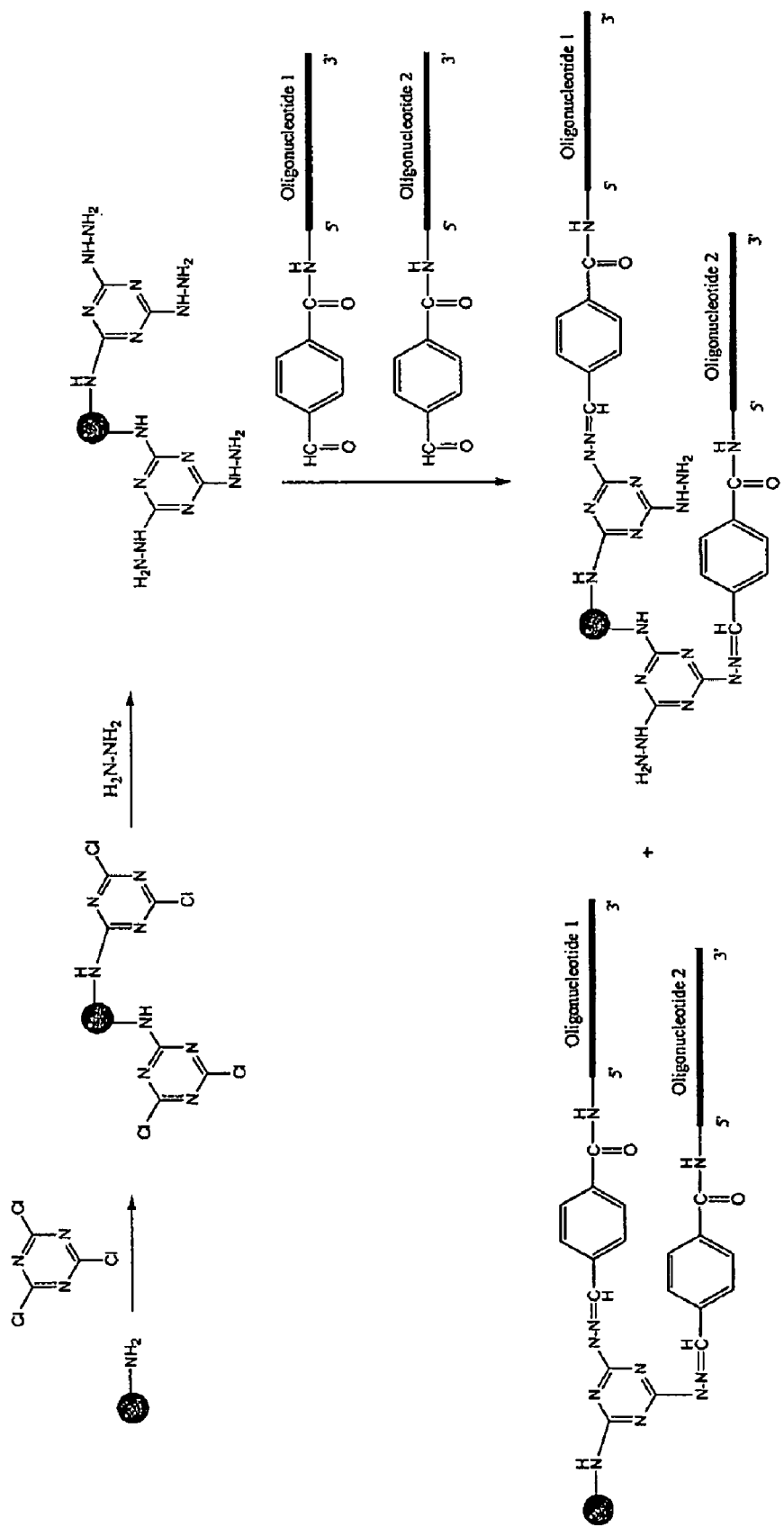
FIG. 2 is a schematic of the one-pot reaction sequence for attaching two oligonucleotides to a bead.

An embodiment of the above methods is depicted in FIG. 2. As shown in FIG. 2, first a solid surface is modified with triazine chloride. The resulting complex is then reacted with hydrazine, whereupon the chloride substituents on the triazine are replaced with hydrazine. Then a mixture of at least two aldehyde-modified oligonucleotides is reacted with the modified solid surface. While in some embodiments both hydrazine substituents react with the oligonucleotides, in other embodiments only one of the hydrazine moieties reacts with an oligonucleotide.

While FIG. 2 and the above discussion relate only to oligonucleotides, it should be understood that the above procedure can be easily modified to attach other types of compounds, such as peptides or small organic molecules, to triazine-modified solid surfaces. Thus, generally, in the first step, an triazine chloride-modified solid surface is reacted with hydrazine, whereby the chloride substituents on the triazine moieties are replaced by hydrazine. The product is then reacted with a mixture of aldehyde-modified compounds to obtain the final product.

EXAMPLES

The examples below are not limiting and are only illustrative of some of the embodiments disclosed herein.

Example 1

Hydrazine Bead Preparation

Cyanuric chloride activated beads were prepared as follows. 10 g of amino-modified beads were suspended with 20 μL of acetonitrile. Then 0.8 mL of N,N-diisopropylethylamine (DiPEA) and 100 mg of cyanuric chloride were added to the bead suspension. The reaction was mixed by vortexing and shaking at room temperature for 2 hrs. After the reaction, the bead solution was centrifuged and the supernatant removed. The beads were then washed with 100 μL of acetonitrile three times.

The beads were washed six times with DMF. For this and the following washes solvent was added to reach 10% bead solid content solution. The beads were shaken with 2% hydrazine solution in DMF overnight at room temperature using 10% bead solid content. Beads were then washed six times with DMF. The hydrazine beads were stored as a 10% bead solid content solution in DMF at room temperature or used directly. In addition to DMF, this chemistry works well with other solvents, such as acetonitrile and ethanol. The hydrazine solution was found to be stable over long storage periods including up to at least 100 hours.

Example 2

Immobilization of Aldehyde Group Containing Oligonucleotides on Hydrazine Beads

Beads were prepared as described in Example 1. Beads were washed one time with 100 mM Na-citrate buffer, 3 M NaCl, pH 5.0. An aldehyde containing oligonucleotide called sequence 13 (25mer, 2-4 nmols of oligonucleotide per one mg of beads) was added to the washed beads in 100 mM Na-citrate buffer, 3 M NaCl, pH 5.0. The mixture was shaken overnight at room temperature using 10% bead solid content. The beads were then washed six times with water, followed by three washes with ethanol. Beads were stored as a 10% bead solid content solution in ethanol.

Example 3

Sequential Immobilization of Amino Group Containing Oligonucleotides and Aldehyde Group Containing Oligonucleotides Using Hydrazine Beads Amino group containing oligonucleotides were reacted at room temperature, overnight, in aqueous buffer with cyanuric chloride modified beads, prepared as described in Example 1. Beads were washed with aqueous buffer and then ethanol. Following attachment of amino group containing oligonucleotides to the beads, aldehyde group containing oligonucleotides were immobilized as described in Example I.

Activity of the beads was evaluated using a hybridization assay in which fluorescently labeled oligonucleotide probes, having sequences complementary to the immobilized oligonucleotides, were hybridized to the beads and detected in a fluorescent activated cell sorter (FACS). When sequential two-attachment chemistry is used, the hybridization intensities for the first (9mer, attached using amino group containing oligonucleotide) and second attachment (13mer, attached using aldehyde group containing oligonucleotide) were affected by the hydrazine concentrations and reaction times of the hydrazine treatment. Hybridization efficiency increased as incubation time increased from 5 minutes to overnight. The FACS hybridization assay was used to determine the effects of different concentrations of hydrazine on hybridization of probes to the 9mer and 13mer. As hydrazine concentration increased from 0.001% to 25%, hybridization of probes to the 9mer decreased, whereas hybridization of probes to the 13mer increased with increasing hydrazine concentration. Roughly equivalent amounts of hybridization of each probe were observed for hydrazine concentrations in the range of 0.5 to 2%.

Example 4

Immobilization of Two Aldehyde Group Containing Oligonucleotides in Parallel

As an alternative to the sequential immobilization methods described in Example 1, one approach is to mix two aldehyde group containing oligonucleotides together in solution with hydrazine beads.

Hydrazine beads were prepared as described in Example I and mixtures of two aldehyde group containing oligonucleotides having lengths of 25, 50 or 75 nucleotides were reacted with the beads under the conditions described in Example 2. Surprisingly, the sequence of the oligonucleotides present in the mixtures did not adversely alter the final ratio of hybridization competent oligonucleotides immobilized on the beads. FACS hybridization assays were run for beads synthesized using different mixtures containing the same first oligonucleotide sequence in the presence of different second oligonucleotide sequences. The results showed that differences in the composition of the second sequence did not significantly alter the efficiency of immobilization for the first oligonucleotide. Similar analyses using mixtures 75mer and 23mer oligonucleotides showed that the efficiency of 75mer immobilization to beads was not altered by differences in the sequence of 23mers in the mixture. Conversely, the efficiency of 23mer immobilization to beads was not altered by differences in the sequence of 75mers in the mixture.

These results indicate that equivalent amounts of different aldehyde group containing oligonucleotides can be immobilized to hydrazine beads using equimolar mixtures of the two oligonucleotides independent of oligonucleotide size or sequence.

Example 5

Synthesis of Aldehyde Group Containing Oligonucleotides

Amine-containing oligonucleotides that were still protected and attached to CPG, were washed three times with 200 µL of acetonitrile. Following the wash, 50 µL of solution containing 0.1 M O-(7-Azabenzotriazol-1-yl)-N,N,N',N'-tetramethyluronium hexafluorophosphate (HATU), 0.1 M 4-carboxybenzaldehyde, and 0.2 M diisopropylethylamine was added to the CPG and incubated for 15 min. The CPG was then washed once with 200 µL of acetonitrile. The sequence of adding the 50 µL reaction solution for a 15 minute reaction and washing in 200 µL was repeated three more times. The oligonucleotide was deprotected with ammonia for 8 hours, extracted and eluted in water Example 6

Attachment of Oligonucleotides to Beads Using Aldehyde Modified Oligonucleotides DNA Synthesis.

Oligonucleotide (oligo) was synthesized on CPG by standard phosphoamidite chemistry using ABI Expedite DNA synthesizer or a proprietary 96-well or 384-well Oligator DNA synthesizer. A formylindole phosphoramidite modifier from Link Technologies was used to introduce an aldehyde residue into the 5' end of the oligonucleotides. After formylindole amidite coupling, the DMT was removed using 100 µL of 3% dichloroacetic acid in dichloromethane at room temperature for 10 minutes, the product was then washed with 1 mL of acetonitrile 3 times. The oligonucleotide was then cleaved off from CPG and deprotected using 100 µL of 28% ammonium hydroxide in water at 55° C. for 8 hours. After cleavage, the solution was dried in a speedvac, and the oligonucleotide was extracted using 100 µL of water.

Triazine Hydrazine Activated Beads Preparation:

Silica beads (1 g) were washed with 10 mL ethanol (HPLC grade). The beads were then suspended in 10 mL ethanol followed by addition of 50 µL (0.5%) 3-aminopropyltrimethoxysilane, and shaken for 1 hour at room temperature. Following silanization they were washed 5 times with 10 mL ethanol and 3 times with 10 mL ether, dried at room temperature. The amino beads (100 mg) were then suspended in acetonitrile (1 mL), followed by addition of 20 µL (0.12 mmol) DIEA (N,N-diisopropylethylamine). After a brief sonication, 10 mg (0.05 mmol) cyanuric chloride was added and the reaction mixture was shaken for 2 hours at room temperature. The beads were washed 3 times with 1 mL acetonitrile.

The cyanuric activated beads were then reacted with 2% hydrazine solution in DMF (acetonitrile can also be used) for 12 hours at room temperature. The beads were washed 6 times with DMF, 3 times with ethanol and stored as 10% solid in ethanol until needed.

Figure 3:
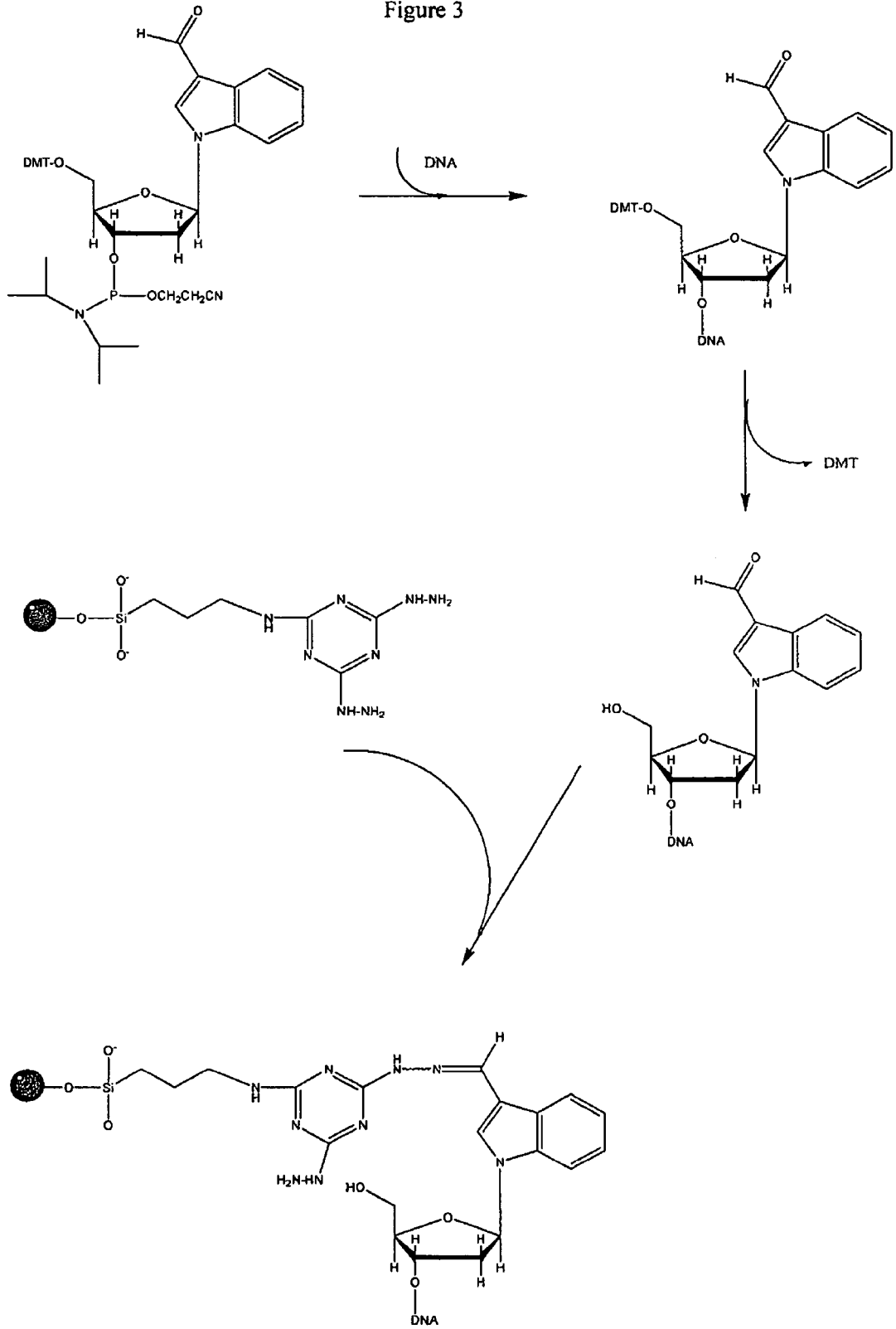
FIG. 3 is a schematic of a reaction sequence for attaching oligonucleotides to a bead.
Figure 4:
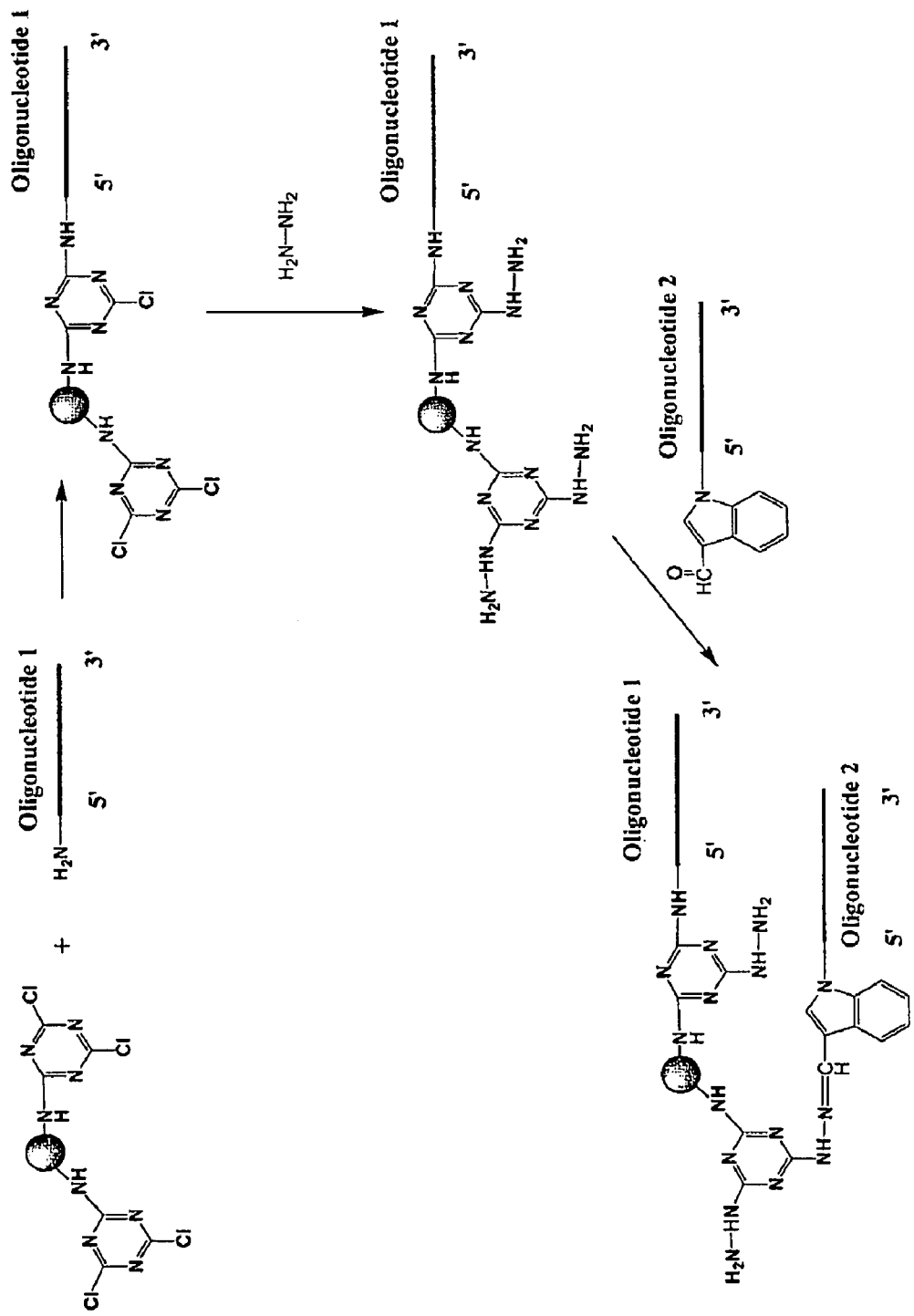
FIG. 4 is another schematic of the two-step reaction sequence for attaching two oligonucleotides to a bead.
Figure 5:
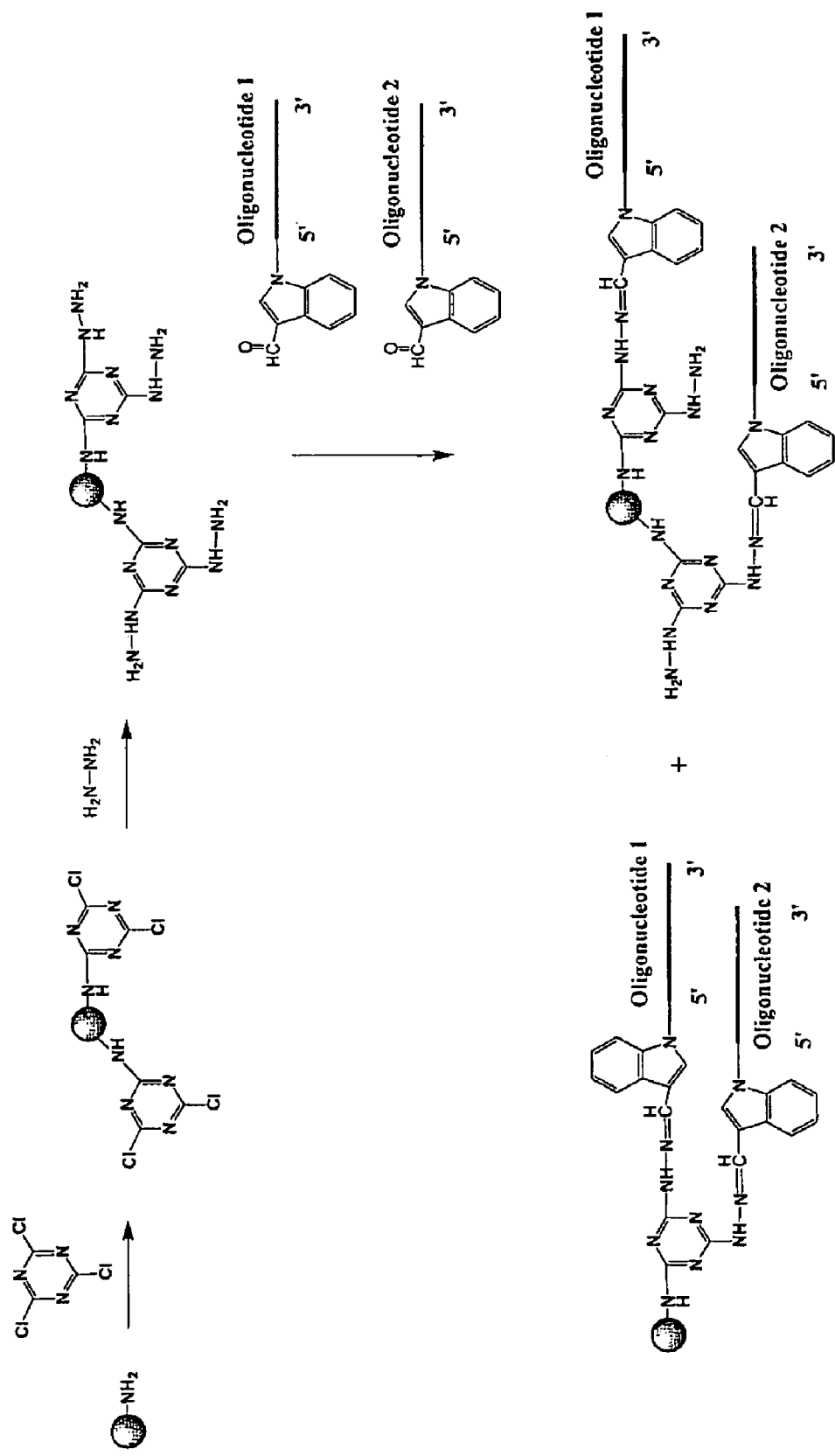
FIG. 5 is another schematic of the one-pot reaction sequence for attaching two oligonucleotides to a bead.

DNA Immobilization:

An aldehyde modified oligonucleotide (100 nmol in 0.1 M sodium citrate/citric acid, pH 5.0) was added to 2 M sodium chloride solution (100 µL). The oligonucleotide solution was added to hydrazine-activated beads (25 mg beads in 100 µL of 0.1 M sodium citrate/citric acid, pH 5.0). The beads were shaken overnight at room temperature and then washed 3 times with water. FIG. 3 is a scheme showing the synthesis of an immobilized DNA molecule using the procedure set forth above.

Throughout this application various publications and patents have been referenced. The disclosure of these publications in their entireties are hereby incorporated by reference in this application in order to more fully describe the state of the art to which this invention pertains.

The term "comprising" is intended herein to be open-ended, including not only the recited elements, but further encompassing any additional elements.

Example 7

Sequential Immobilization of Amino Group Containing Oligonucleotides and Aldehyde Group Containing Oligonucleotides Using Hydrazine Beads Amino group containing oligonucleotides were reacted at room temperature, overnight, in aqueous buffer with cyanuric chloride modified beads, prepared as described in Example 1. Beads were washed with aqueous buffer and then ethanol. Following attachment of amino group containing oligonucleotides to the beads, aldehyde group containing oligonucleotides were immobilized as described in Example I.

Activity of the beads was evaluated using a hybridization assay in which fluorescently labeled oligonucleotide probes, having sequences complementary to the immobilized oligonucleotides, were hybridized to the beads and detected in a fluorescent activated cell sorter (FACS). When sequential two-attachment chemistry is used, the hybridization intensities for the first 23-mer, oligonucleotide 1, attached using amino group containing oligonucleotide and second 23-mer, oligonucleotide 2, attached using aldehyde group containing oligonucleotide were affected by the hydrazine concentrations and reaction times of the hydrazine treatment. Hybridization efficiency increased as incubation time increased from 5 minutes to overnight. The FACS hybridization assay was used to determine the effects of different concentrations of hydrazine on hybridization of probes to the oligonucleotide 1 and oligonucleotide 2. As hydrazine concentration increased from 0.001% to 25%, hybridization of probes to the 23-mer, oligonucleotide 1 decreased, whereas hybridization of probes to the 23-mer, oligonucleotide 2 increased with increasing hydrazine concentration. Roughly equivalent amounts of hybridization of each probe were observed for hydrazine concentrations in the range of 0.5 to 2%.

What is claimed is:
1. A compound of the Formula XXVII:

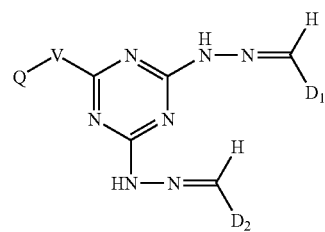

(XXVII)

wherein
- $D_1$ and $D_2$ are the same or different biologically active polymers;
- Q is a solid surface;
- V is selected from the group consisting of a bond, $SiO_3$, NH, CO, NHCO, C(O)NH, $(CH_2)_p$, sulfur, and oxygen, or a combination thereof; and
- p is an integer greater than or equal to zero.

2. The compound of claim 1, wherein V is NH.

3. The compound of claim 1, wherein V is —NH—$(CH_2)_p$—Si(O)$_3$ and p is an integer greater than or equal to zero.

4. The compound of claim 1, wherein $D_1$ is selected from the group consisting of RNA, DNA, a polypeptide, RNA having one or more non-naturally occurring bases, DNA having one or more non-naturally occurring bases, and a polypeptide having one or more non-naturally occurring amino acids.

5. The compound of claim 1, wherein $D_2$ is selected from the group consisting of RNA, DNA, a polypeptide, RNA having one or more non-naturally occurring bases, DNA having one or more non-naturally occurring bases, and a polypeptide having one or more non-naturally occurring amino acids.

6. The compound of claim 1, wherein Q is selected from the group consisting of resin, microbead, glass, controlled pore glass (CPG), polymer support, membrane, paper, plastic, plastic tube or tablet, plastic bead, glass bead, slide, ceramic, silicon chip, multi-well plate, nylon membrane, and PVDF membrane.

7. The compound of claim 1, wherein $D_1$ is DNA.

8. The compound of claim 1, wherein $D_2$ is DNA.

9. The compound of claim 1, wherein Q is a glass bead.

10. The compound of claim 1, wherein V is NH, at least one of $D_1$ and $D_2$ is DNA and Q is a glass bead.

11. The compound of claim 1, wherein V is NH, both $D_1$ and $D_2$ are DNA and Q is a glass bead.

12. The compound of claim 1, wherein V is NH, at least one of $D_1$ and $D_2$ is DNA and Q is controlled pore glass (CPG).

13. The compound of claim 1, wherein V is NH, both $D_1$ and $D_2$ are DNA and Q is controlled pore glass (CPG).

14. The compound of claim 1, wherein V is —NH—$(CH_2)_p$—Si(O)$_3$, p is an integer greater than or equal to zero and Q is a glass bead.

15. The compound of claim 1, wherein V is —NH—$(CH_2)_p$—Si(O)$_3$, p is an integer greater than or equal to zero and Q is controlled pore glass (CPG).

16. The compound of claim 1, wherein V is NH, at least one of $D_1$ and $D_2$ is DNA and Q is controlled pore glass (CPG).

17. The compound of claim 1, wherein V is NH, both $D_1$ and $D_2$ are DNA and Q is controlled pore glass (CPG).

18. The compound of claim 1, wherein V is —NH—$(CH_2)_p$—Si(O)$_3$, p is an integer greater than or equal to zero, at least one of $D_1$ and $D_2$ is DNA and Q is a microbead.

19. The compound of claim 1, wherein V is —NH—$(CH_2)_p$—Si(O)$_3$, p is an integer greater than or equal to zero and Q is a silicon chip or multi-well plate.

20. The compound of claim 1, wherein V is —NH—$(CH_2)_p$—Si(O)$_3$, p is an integer greater than or equal to zero and Q is a silicon chip or multi-well plate.

21. The compound of claim 1, wherein V is NH, at least one of $D_1$ and $D_2$ is DNA and Q is a silicon chip or multi-well plate.

22. The compound of claim 1, wherein V is NH, both $D_1$ and $D_2$ are DNA and Q is a silicon chip or multi-well plate.

23. The compound of claim 1, wherein V is —NH—$(CH_2)_p$—Si(O)$_3$, p is an integer greater than or equal to zero, at least one of $D_1$ and $D_2$ is DNA and Q is a silicon chip or multi-well plate.

* * * * *